(12) United States Patent
Dop

(10) Patent No.: US 9,050,270 B2
(45) Date of Patent: Jun. 9, 2015

(54) COSMETIC METHOD USING A COMPOSITION CONTAINING SILOXANE RESINS AND FILLERS

(75) Inventor: Florence Dop, Villers le Bacle (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 13/132,173

(22) PCT Filed: Dec. 2, 2009

(86) PCT No.: PCT/FR2009/052387
§ 371 (c)(1),
(2), (4) Date: Jun. 1, 2011

(87) PCT Pub. No.: WO2010/063960
PCT Pub. Date: Jun. 10, 2010

(65) Prior Publication Data
US 2012/0014899 A1    Jan. 19, 2012

Related U.S. Application Data

(60) Provisional application No. 61/120,863, filed on Dec. 9, 2008.

(30) Foreign Application Priority Data

Dec. 2, 2008 (FR) ...................... 08 58195

(51) Int. Cl.
*A61K 8/58* (2006.01)
*A61K 31/74* (2006.01)
*A61K 8/06* (2006.01)
*A61K 8/891* (2006.01)
*A61K 8/894* (2006.01)
*A61Q 1/02* (2006.01)
*A61Q 1/06* (2006.01)
*A61Q 1/10* (2006.01)
*A61Q 1/12* (2006.01)

(52) U.S. Cl.
CPC . *A61K 8/585* (2013.01); *A61K 8/06* (2013.01); *A61K 8/064* (2013.01); *A61K 8/891* (2013.01); *A61K 8/894* (2013.01); *A61K 2800/594* (2013.01); *A61Q 1/02* (2013.01); *A61Q 1/06* (2013.01); *A61Q 1/10* (2013.01); *A61Q 1/12* (2013.01)

(58) Field of Classification Search
CPC ... A61K 2800/594; A61K 8/06; A61K 8/064; A61K 8/585; A61K 8/891; A61K 8/894; A61K 8/1585; A61Q 1/02; A61Q 1/06; A61Q 1/10; A61Q 1/12
USPC .......................................... 424/70.121, 78.03
See application file for complete search history.

(56) References Cited

U.S. PATENT DOCUMENTS

| | | | |
|---|---|---|---|
| 6,964,773 B1* | 11/2005 | Morrison | 424/401 |
| 2006/0177401 A1* | 8/2006 | Themens et al. | 424/70.12 |
| 2007/0166271 A1* | 7/2007 | Gordon et al. | 424/70.122 |
| 2008/0171006 A1 | 7/2008 | Bui et al. | |
| 2012/0003167 A1 | 1/2012 | Cavazzuti et al. | |

OTHER PUBLICATIONS

U.S. Appl. No. 13/132,497, filed Dec. 16, 2011, Barba, et al.
U.S. Appl. No. 13/132,085, filed Sep. 16, 2011, Cavazzuti, et al.
Kowandy, V. et al., "Bodied MQ-T Propyl Silicone Resins in Color Cosmetic Applications", ip.com Journal, Total 16 Pages, XP-013127272, (Dec. 4, 2008).
International Search Report Issued Jun. 9, 2010 in PCT/FR09/052387 filed Dec. 2, 2009.
French Search Report Issued Jun. 24, 2009 in French Patent Application No. 08 58195 filed Dec. 2, 2008.
U.S. Appl. No. 13/132,214, filed Jun. 1, 2011, Dop.
U.S. Appl. No. 13/132,203, filed Jun. 1, 2011, Dop.
U.S. Appl. No. 13/132,195, filed Jun. 1, 2011, Dop.

* cited by examiner

*Primary Examiner* — Anna Pagonakis
*Assistant Examiner* — Miriam A Levin
(74) *Attorney, Agent, or Firm* — Oblon, McClelland, Maier & Neustadt, L.L.P.

(57) ABSTRACT

The invention relates to a cosmetic method for making-up and/or caring for keratin materials, in particular the skin, whereby a cosmetic composition is applied to the keratin materials, said cosmetic composition comprising siloxane resins and fillers. In particular, the invention relates to compositions used to care for or make-up the aforementioned keratin materials.

16 Claims, No Drawings

COSMETIC METHOD USING A COMPOSITION CONTAINING SILOXANE RESINS AND FILLERS

The invention relates to a cosmetic method for making up and/or caring for keratin materials, in particular the skin, comprising the application to said keratin materials of a cosmetic composition comprising siloxane resins and fillers. The invention relates in particular to compositions for caring for or making up said keratin materials.

It is known practice to use makeup products in order to bring color and mattness to the skin. These makeup products are expected to provide a makeup result which holds during the day.

A makeup product should also be comfortable. The term "comfortable" is intended to mean a product which glides on the skin, without any sensation of rubbing when the product is applied to the skin, but also a product which gives said skin a soft feel.

It is known to those skilled in the art to confer comfort properties on a makeup product, as is described above, by formulating these products with fillers.

It is also known to those skilled in the art to confer makeup staying-power properties by formulating these products with silicone resins, polyacrylates, or else latexes, which have, however, a tendency to cause a feeling of discomfort after application, with a tacky feel.

The aim of the present invention is therefore to provide a makeup method which makes it possible to obtain satisfactory makeup staying power properties, and in particular a satisfactory mattifying effect, while at the same time being comfortable during and after application.

This objective, and also others, are achieved by means of the present invention which describes in particular a cosmetic method for making up and/or caring for keratin materials, comprising the application, to said keratin materials, in particular to the skin, of a composition comprising, in a physiologically acceptable medium:

a) a siloxane resin comprising at least 80 mol % of units:
  (i) $(R'_3SiO_{1/2})_a$ (hereinafter "M" units) and
  (ii) $(SiO_{4/2})_b$ (hereinafter "Q" units)
  in which
    R' independently represents an alkyl group containing from 1 to 8 carbon atoms, an aryl group, a carbinol group or an amino group,
  with the condition that at least 95 mol % of the R' groups are alkyl groups,
    a and b are values strictly greater than 0,
    and the ratio a/b is between 0.5 and 1.5;
b) a propyl silsesquioxane resin comprising at least 80 mol % of $(R''SiO_{3/2})$ units (hereinafter "T" units) in which R" independently represents an alkyl group containing from 1 to 8 carbon atoms, an aryl group, a carbinol group or an amino group, with the condition that at least 80 mol % of the R" groups are propyl groups;
  the weight ratio between the resins a) and b) being between 1/99 and 99/1, in particular between 85/15 and 15/85,
  the resins a) and b) not being bonded to one another via covalent bonds,
  and the number of M units in the final mixture being strictly less than the number of (T+Q) units;
and
c) at least one mineral filler and at least one other mineral or organic filler.

A subject of the present invention is also a cosmetic method for making up and/or caring for keratin materials, comprising the application, to said keratin materials, of a composition comprising, in a physiologically acceptable medium:
a) a siloxane resin comprising at least 80 mol % of units:
  (i) $(R'_3SiO_{1/2})_a$ (hereinafter "M" units) and
  (ii) $(SiO_{4/2})_b$ (hereinafter "Q" units)
  in which
    R' independently represents an alkyl group containing from 1 to 8 carbon atoms, an aryl group, a carbinol group or an amino group, with the condition that at least 95 mol % of the R' groups are alkyl groups,
    a and b are values strictly greater than 0,
    and the ratio a/b is between 0.5 and 1.5;
b) a film-forming propyl silsesquioxane resin comprising at least 80 mol % of $(R''SiO_{3/2})$ units (hereinafter "T" units) in which R" independently represents an alkyl group containing from 1 to 8 carbon atoms, an aryl group, a carbinol group or an amino group, with the condition that at least 40 mol % of the R" groups are propyl groups,
  the weight ratio between the resins a) and b) being between 1/99 and 99/1, in particular between 85/15 and 15/85,
  the resins a) and b) not being bonded to one another via covalent bonds, and the number of M units in the final mixture being strictly less than the number of (T+Q) units;
and
c) at least one mineral filler and at least one other mineral or organic filler.

The combination used according to the invention makes it possible to obtain a soft finish on the skin and cosmetic properties which stable over time, in particular throughout the day. The product also glides on the skin, during application, without any sensation of rubbing, and gives said skin a soft feel.

The composition according to the invention may be in various forms, in particular in the form of powders (loose or compact), of an anhydrous dispersion, of a water/oil or water/wax emulsion, an oil/water emulsion, multiple emulsions (such as a water/oil/water or oil/water/oil emulsion) or wax/water emulsion, or else in the form of a gel. Preferably, the composition according to the invention is in the form of powders (loose or compact), of an anhydrous dispersion or of emulsions, preferably an inverse emulsion (i.e. water/oil emulsion).

The composition according to the invention is in particular intended for making up and/or caring for the skin.

Siloxane Resins

The siloxane resin a), subsequently referred to as "MQ resin", preferably comprises residual silanol groups (—SiOH). In this case, the amount of —OH groups is preferably between 2% and 10% by weight of the MQ resin, preferably between 2% and 5% by weight of the MQ resin.

Preferably, the R' groups of the MQ resin are methyl groups.

The resin b), hereinafter referred to as "propyl T resin", preferably comprises residual silanol groups (—SiOH) and/or alkoxy groups. In this case, the amount of —OH groups is preferably between 2% and 10% by weight of the propyl T resin, and/or the amount of alkoxy groups is preferably less than or equal to 20% by weight of the propyl T resin. Preferably, the amount of —OH groups is between 6% and 8% by weight of the propyl T resin, and/or the amount of alkoxy groups is less than or equal to 10% by weight of the propyl T resin.

The propyl T resin according to the invention is such that at least 40 mol % of the R" groups are propyl groups, preferably at least 50 mol %, and more preferentially at least 90 mol %.

The term "covalent bond" is intended to mean a chemical bond between at least two atoms (carbon, silicon, oxygen, etc.) in which each of the atoms bonded pools one electron from one of its outer layers in order to form a doublet of electrons linking the two atoms.

The MQ resin according to the invention comprises at least 80 mol % of units:
  (i) $(R'_3SiO_{1/2})_a$ (hereinafter "M" units) and
  (ii) $(SiO_{4/2})_b$ (hereinafter "Q" units), in which
R' independently represents an alkyl group containing from 1 to 8 carbon atoms, an aryl group, a carbinol group or an amino group,
with the condition that at least 95 mol % of the R' groups are alkyl groups,
a and b are values strictly greater than 0,
and the ratio a/b is between 0.5 and 1.5.

The R' radical of the MQ resin independently represents an alkyl group containing from 1 to 8 carbon atoms, an aryl group, a carbinol group or an amino group.

The alkyl groups may in particular be chosen from methyl, ethyl, propyl, butyl, pentyl, hexyl and octyl groups. Preferably, the alkyl group is a methyl or propyl group.

The aryl groups may be chosen from phenyl, naphthyl, benzyl, tolyl, xylyl, xenyl, methylphenyl, 2-phenylethyl, 2-phenyl-2-methylethyl, chlorophenyl, bromophenyl and fluorophenyl groups, the aryl group being preferentially a phenyl group.

In the present invention, the term "carbinol group" is intended to mean any group containing at least one hydroxyl radical bonded to a carbon (COH). The carbinol groups may thus contain more than one COH radical, such as, for example

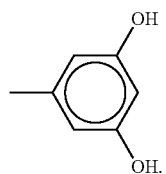

If the carbinol group is free of aryl groups, it contains at least 3 carbon atoms.

If the carbinol group comprises at least one aryl group, it contains at least 6 carbon atoms.

As examples of carbinol groups free of aryl groups, containing at least 3 carbon atoms, mention may be made of groups of formula $R^1OH$ in which $R^1$ represents a divalent hydrocarbon-based radical containing at least 3 carbon atoms or a divalent hydrocarbonoxy radical containing at least 3 carbon atoms. As examples of an $R^1$ group, mention may be made of alkylene radicals, such as —$(CH_2)_x$—, the value of x being between 3 and 10, —$CH_2CH(CH_3)$—, —$CH_2CH(CH_3)CH_2$—, —$CH_2CH_2CH(CH_2CH_3)CH_2CH_2CH_2$— and —$OCH(CH_3)(CH_2)_x$—, the value of x being between 1 and 10.

As examples of a carbinol group comprising aryl groups, having at least 6 carbon atoms, mention may be made of groups of formula $R^2OH$ in which $R^2$ represents an arylene radical, such as —$(CH_2)_xC_6H_4$—, x having a value of between 0 and 10, —$CH_2CH(CH_3)(CH_2)_xC_6H_4$—, x having a value between 0 and 10, and —$(CH_2)_xC_6H_4(CH_2)_x$—, x having a value between 1 and 10. The carbinol groups comprising aryl groups generally contain from 6 to 14 atoms.

According to the invention, the term "amino group" is intended to mean in particular groups of formula —$R^3NH_2$ or —$R^3NHR^4NH_2$, $R^3$ representing a divalent hydrocarbon-based radical containing at least two carbon atoms and $R^4$ representing a divalent hydrocarbon-based radical containing at least 2 carbon atoms. The $R^3$ group generally represents an alkylene radical containing from 2 to 20 carbon atoms. As examples of an $R^3$ group, mention may be made of ethylene, propylene, —$CH_2CHCH_3$—, butylene, —$CH_2CH(CH_3)CH_2$—, pentamethylene, hexamethylene, 3-ethylhexamethylene, octamethylene and decamethylene groups.

The $R^4$ group generally represents an alkylene radical containing from 2 to 20 carbon atoms. As examples of an $R^4$ group, mention may be made of ethylene, propylene, —$CH_2CHCH_3$—, butylene, —$CH_2CH(CH_3)CH_2$—, pentamethylene, hexamethylene, 3-ethylhexamethylene, octamethylene and decamethylene groups.

The amino groups are generally —$CH_2CH_2CH_2NH_2$ and —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$ and —$CH_2CH_2NHCH_2CH_2NHC_4H_9$.

MQ resins that are suitable for use as component a), and also the methods for the production thereof, are known in the prior art. U.S. Pat. No. 2,814,601, belonging to Currie et al., of Nov. 26, 1957, incorporated into the present document by way of reference, describes a method for the production of MQ resins by conversion of a water-soluble silicate into a silicic acid monomer or a silicic acid oligomer using an acid. Once the appropriate polymerization has been carried out, trimethylchlorosilane ends are introduced in order to obtain the MQ resin. Another method for preparing MQ resins is described in U.S. Pat. No. 2,857,356 belonging to Goodwin, of Oct. 21, 1958, incorporated into the present document by way of reference. Goodwin describes a method for the production of an MQ resin by cohydrolysis of a mixture of an alkyl silicate and an organopolysiloxanetrialkylsilane which is hydrolysable, with water.

The MQ resins that are suitable as component a) in the present invention can contain D and T units, provided that at least 80 mol %, or even 90 mol %, of the total siloxane units are M and Q units. The MQ resins can also contain residual hydroxyl groups as is mentioned above. The MQ resins can also comprise additional ends, residual hydroxyl groups being, for this, reacted with suitable M groups.

The propyl T resin b) according to the invention comprises at least 80 mol % of (R"SiO$_{3/2}$) units in which R" independently represents an alkyl group containing from 1 to 8 carbon atoms, an aryl group, a carbinol group or an amino group, with the condition that at least 40 mol % of the R" groups are propyl groups.

Preferably, the propyl T resin according to the invention is such that at least 50 mol % of the R" groups are propyl groups, preferably at least 90 mol %.

Preferably, the propyl T resin b) is film-forming. The term "film-forming resin" is intended to mean a resin capable of forming, by itself or in the presence of an auxiliary film-forming agent, a film which is macroscopically continuous and adherent to keratin materials, and preferably a cohesive film, and even better still a film of which the cohesion and the mechanical properties are such that it is possible for said film to be isolated and to be handled in isolation, for example when said film is produced by pouring onto a non-stick surface such as a Teflon-coated or silicone-coated surface.

The definition of the R" radical is the same as that of the R' radical. The definitions mentioned above that are applicable to R' are thus applicable to R".

The propyl T resin b) according to the invention is a silsesquioxane resin. Silsesquioxane resins are well known in the prior art and are generally obtained by hydrolysis of an organosilane comprising three hydrolysable groups, such as halogen or alkoxy groups, present in the molecule. The propyl T resin b) can thus be obtained by hydrolysis of propyltrimethoxysilane, propyltriethoxysilane or propyltripropoxysilane, or by cohydrolysis of the abovementioned propylalkoxysilanes with various alkoxysilanes. As examples of these alkoxysilanes, mention may be made of methyltrimethoxysilane, methyltriethoxysilane, methyltriisopropoxysilane, dimethyldimethoxysilane and phenyltrimethoxysilane. Propyltrichlorosilane can also be hydrolyzed alone, or in the presence of alcohol. In this case, the cohydrolysis can be carried out by adding methyltrichlorosilane, dimethyldichlorosilane, phenyltrichlorosilane or similar chlorosilanes and methyltrimethoxysilane, methyltriethoxysilane, methyltriisopropoxysilane or similar methylalkoxysilanes. As alcohols that are suitable for this purpose, mention may be made of methanol, ethanol, n-propyl alcohol, isopropyl alcohol, butanol, methoxyethanol, ethoxyethanol or similar alcohols. As examples of hydrocarbon-type solvents that can be used simultaneously, mention may be made of toluene, xylene or similar aromatic hydrocarbons, hexane, heptane, isooctane or similar linear or partially branched, saturated hydrocarbons; and also cyclohexane or similar aliphatic hydrocarbons.

The propyl T resins b) according to the invention may contain M, D and Q units, provided that at least 80 mol %, or even 90 mol %, of the total siloxane units are T units. The propyl T resins may also contain residual hydroxyl and/or alkoxy groups, as is mentioned above.

The composition according to the invention also comprises a physiologically acceptable medium. The term "physiologically acceptable medium" is intended to mean a medium that is compatible with the skin, the mucous membranes and the skin integuments.

This medium may comprise at least one volatile silicone or organic solvent, this solvent preferably being compatible with the resins a) and b) and compatible with cosmetic use.

As volatile silicone solvent, mention may be made of cyclic polysiloxanes, linear polysiloxanes and mixtures thereof.

As volatile linear polysiloxanes, mention may be made of hexamethyldisiloxane, octamethyltrisiloxane, decamethyltetrasiloxane, tetradecamethylhexasiloxane and hexadecamethylheptasiloxane.

As volatile cyclic polysiloxanes, mention may be made of hexamethylcyclotrisiloxane, octamethylcyclotetrasiloxane, decamethylcyclopentasiloxane and dodecamethylcyclohexasiloxane.

The organic solvent may also be an alcohol, for instance ethanol, isopropanol, butanol, n-propanol; a ketone, for instance acetone, methyl ethyl ketone, or methyl isobutyl ketone; an aliphatic hydrocarbon, for instance heptane, hexane, octane or isododecane, or a glycol ether, for instance propylene glycol methyl ether, dipropylene glycol methyl ether, propylene glycol n-butyl ether, propylene glycol n-propyl ether, or ethylene glycol n-butyl ether.

The mixture of resins a) and b) may be obtained from each of the resins in solution in a solvent.

In general, at the end of synthesis of the MQ resin according to the invention, this resin is obtained directly in solution in xylene.

Likewise, at the end of synthesis of the propyl T resin b) according to the invention, this resin is obtained in solution in toluene.

Each of these resins in solution is mixed with the other one according to the following protocol:
1) the two resin solutions are mixed, with stirring, and then heated, in particular in a reactor or in an autoclave (in order to be able to carry out the operation optionally under pressure or, on the contrary, by establishing a partial vacuum), or even in an extruder optionally equipped with a solvent "devolatilization" system, under the following specific conditions:
   uniform heating is carried out: the heating temperature should be greater than 90° C., and less than or equal to 250° C., and preferably between 90° C. and 190° C.
   Either the heating can be carried out at a single temperature, of between 90° C. and 250° C.,
   or the heating can be carried out by performing successive temperature holds:
   first between 90° C. and T1° C.,
   T1° C. being a temperature having an intermediate value of between 90° C. and T2° C. which is the final temperature,
   for a period of time of between 10 minutes and 2 hours, and then between 11° C. and T2° C., for a period of time of between 10 minutes and 4 hours,
   the temperature T2° C. corresponding to the maximum temperature chosen for the reaction.
   This value of T2° C. is variable according to the procedure chosen and the type of reactor chosen: conventional reactor or autoclave or extruder, but T2° C. remains less than or equal to 250° C. It is also possible to perform intermediate temperature holds between T1° C. and T2° C.;
   the heating time is at least one hour in a reactor or in an autoclave and at least 10 minutes in an extruder, preferably between 1 h and 5 h in a reactor or in an autoclave, and preferably between 10 minutes and 2 hours in an extruder;
   provided that these heat treatments are carried out without the presence of a catalyst for chemical condensation between the two MQ and propyl T resins. Such a catalyst is in particular a mineral base, in particular NaOH, KOH or aqueous ammonia.
2) Optionally, after, or even during, step 1) of heat treatment of the two resins in the temperature range indicated, partial or total distillation of the aromatic solvents is carried out, replacing them with a cosmetically acceptable volatile solvent. Such a volatile solvent may in particular be a volatile silicone, or not, preferably decamethylcyclopentasiloxane, or a volatile organic solvent, or not, preferably isododecane.
3) Again optionally, after mixing of the two initial solutions of each resin in a volatile solvent, the mixture of solutions is treated in a screw or twin-screw blender of "devolatilizing" extruder type, in a temperature range between 90° C. and 250° C., making it possible to volatilize the volatile solvents by establishing a partial vacuum, while working continuously, and then to pass the molten mixture without solvent through a die. The molten mixture is then cooled on leaving the die and cut up in solid granules or in the form of a powder. In this case, the mixture is directly in solid form and will be redissolved in the selected solvents at the time of formulation.

Thus, a subject of the present invention is also a composition as described above, comprising, in a physiologically acceptable medium:
1) the mixture of a siloxane resin a) and a propyl silsesquioxane resin b), the mixture being as described above, and
2) at least one volatile C8 to C16 hydrocarbon-based solvent, the siloxane resin a) and the propyl silsesquioxane resin b) being formulated in the composition via a mixture that can be obtained according to the following method:
   mixing, preferably with stirring, a solution of siloxane resin with a solution of propyl silsesquioxane resin, the solvent present in each of the solutions preferably being volatile, and then
   heating, in particular in a reactor or in an autoclave or in an extruder, under the following specific conditions:
   heating is carried out uniformly at a temperature of greater than 90° C., and less than or equal to 250° C., preferably between 90° C. and 190° C.; the heating can be carried out at a single temperature, or at temperature holds, as indicated above;
   the heating time is at least 1 hour in a reactor or in an autoclave and at least 10 minutes in an extruder, preferably between 1 h and 5 h in a reactor or in an autoclave and preferably between 10 minutes and 2 hours in an extruder;
   provided that these heat treatments are carried out without the presence of a catalyst for chemical condensation between the two MQ and propyl T resins. Such a catalyst is in particular a mineral base, in particular NaOH, KOH or aqueous ammonia.

This method may comprise, after or even during the mixing step, an additional step of partial or total distillation of the aromatic solvents, replacing them with a cosmetically acceptable volatile solvent.

When an extruder is used, this method may comprise, after or even during the mixing step, an additional step of partial or total distillation of the aromatic solvents, with the mixture exiting directly in the solid state.

The final step of the heat treatment, or even the heat treatment itself, can be carried out in a blender intended for stirring very viscous media, such as:

a "Z-arm" blender ("Zigma blender"), in particular a Brabender blender, an extruder-type screw blender, in particular a single-screw extruder or a twin-screw extruder (with or without a step of "devolatilization" of the starting volatile solvents) or in a kneader which makes it possible to devolatilize by establishing a thin film on the walls.

The mixtures of resins that can be used according to the invention are in particular those described in application WO 2005/075567, the content of which is incorporated herein by way of reference, in particular those described in tables 1 and 3 of said application. It is also possible to use the mixtures of resins 1) described in application WO 2007/145765, in particular those described in examples 12 to 14 of that application, in which the weight ratio between the resins a) and b) is respectively 50/50, 60/40 and 71/29 (70/30).

According to one particular embodiment, the mixture of resins 1) described in example 1-f in table 1 of the examples, in which the weight ratio between the resins a) and b) is 50/50, is used.

According to one particular embodiment, the mixture of resins 1) described in example 22 of said application WO 2005/075567, in which the weight ratio between the resins a) and b) is 85/15, is used.

According to one particular embodiment, the mixture of resins 1) described in example 13 of said application WO 2007/145765, in which the weight ratio between the resins a) and b) is 60/40, is used.

The weight ratio between the resins a) and b) (i.e. a/b) is between 1/99 and 99/1, alternatively between 85/15 and 15/85.

The composition according to the invention comprises an amount of siloxane resins a) and b), by weight of active material (dry matter), ranging from 0.5% to 60% by weight, relative to the total weight of the composition, preferably from 3% to 60% by weight, and better still from 4% to 60% by weight, relative to the total weight of said composition.

According to one particular embodiment, the amount of siloxane resins a) and b), by weight of active material (dry matter) advantageously ranges from 3% to 60% by weight, and better still from 6% to 60% by weight, relative to the total weight of said composition. These contents are in particular suitable for compositions in anhydrous form, and in particular for compositions in the form of a stick, such as lipsticks.

According to another particular embodiment, the amount of siloxane resins a) and b), by weight of active material (dry matter), ranges advantageously from 3% to 30% by weight, and better still from 4% to 20% by weight, relative to the total weight of said composition. These contents are especially suitable for compositions in the form of emulsions, and in particular for compositions in the form of W/O emulsions, such as liquid foundations.

Filler

The composition according to the invention comprises one or more fillers, in particular at least one mineral filler and at least one other mineral or organic filler.

The term "mineral fillers" should be understood to mean colorless or white, lamellar or nonlamellar mineral particles. The mineral fillers may be of any shape, such as in particular potatoid, lamellar, platelet, spherical or oblong. They can be of any crystallographic form (for example sheet, cubic, hexagonal, orthorhombic, etc.). Mention may in particular be made of talc, mica, silica, kaolin, boron nitride, precipitated calcium carbonate, magnesium carbonate, magnesium hydrogen carbonate, hydroxyapatite, hollow silica microspheres (Silica Beads® from Maprecos), or glass or ceramic microcapsules, clay, quartz, natural diamond powder, or mixtures thereof.

As silica powder, mention may be made of:

the porous silica microspheres sold under the name Silica Beads SB-700 by the company Myoshi; Sunsphere® H51 and Sunsphere® H33 by the company Asahi Glass;

the polydimethylsiloxane-coated amorphous silica microspheres sold under the names SA Sunsphere® H 33 and SA Sunsphere® H53 by the company Asahi Glass.

Preferably, the mineral filler is silica, talc or a mixture thereof.

Among the spherical fillers, silicas, for instance hollow silica microspheres, in particular the SB700® from Miyoshi Kasei, are preferred.

According to one variant of the invention, the composition comprises at least one mineral filler of potatoid shape (i.e. a surface shape which has an irregular contour which invokes the longitudinal cross section of a potato), lamellar shape, or a mixture thereof.

The mineral fillers may be present in the composition in a content that can vary to a large extent depending on the nature of the mineral fillers and also depending on the desired product and/or the desired effects; this amount is to be adjusted by those skilled in the art.

The mineral filler(s) may be present in the composition in a content ranging from 0.01% to 50% by weight, in particular from 0.01% to 30% by weight, relative to the total weight of the composition, preferably ranging from 0.01% to 20% by weight.

More specifically, the mineral filler(s) may be present in the composition in a content ranging from 1% to 50% by weight, relative to the total weight of the composition, and better still from 2% to 35% by weight.

The composition according to the invention also comprises at least one other filler.

Said at least one other filler may be mineral or organic. It may thus be a mixture of mineral and organic fillers.

According to one alternative, the composition according to the invention may contain a mineral filler and another mineral filler, said mineral fillers being as defined above, and optionally at least one organic filler, as defined below.

According to another alternative, the composition according to the invention may contain a mineral filler and an organic filler.

The term "organic fillers" should be understood to mean lamellar or nonlamellar, colorless or white organic particles. Mention may in particular be made of polyamide (Nylon® or Orgasol® from Arkema) powders, acrylic polymer powders, in particular polymethyl methacrylate powders, polymethyl methacrylate/ethylene glycol dimethacrylate powders, polyallyl methacrylate/ethylene glycol dimethacrylate powders, ethylene glycol dimethacrylate/lauryl methacrylate copolymer powders, cellulose, poly-β-alanine and polyethylene powders, tetrafluoroethylene polymer (Teflon®), powders, lauroyllysine, starch, polymeric hollow microspheres such as those of polyvinylidene chloride/acrylonitrile, for instance Expancel® (Nobel Industrie), or of acrylic acid copolymers (Polytrap® from the company Dow Corning), and silicone resin microbeads (Tospearls® from Toshiba, for example), elastomeric polyorganosiloxane particles, in particular obtained by polymerization of organopolysiloxane having at least two hydrogen atoms each bonded to a silicon atom and of an organopolysiloxane comprising at least two ethylenically unsaturated groups (in particular two vinyl groups) in the presence of a platinum catalyst, or else metal soaps derived from organic carboxylic acids containing from 8 to 22 carbon atoms, preferably from 12 to 18 carbon atoms, for example zinc stearate, magnesium stearate or lithium stearate, zinc laurate or magnesium myristate.

As acrylic polymer powder, mention may be made of:
the polymethyl methacrylate powders sold under the name Covabead® LH85 by the company Wackherr;
the polymethyl methacrylate/ethylene glycol dimethacrylate powders sold under the name Dow Corning 5640 Microsponge® Skin Oil Adsorber by the company Dow Corning; Ganzpearl® GMP-0820 by the company Ganz Chemical;
the polyallyl methacrylate/ethylene glycol dimethacrylate powders sold under the name Poly-Pore® L200 and Poly-Pore® E200 by the company Amcol;
the ethylene glycol dimethacrylate/lauryl methacrylate copolymer powders sold under the name Polytrap® 6603 by the company Dow Corning.

As elastomeric silicone powder, mention may be made of the powders sold under the names Trefil® Powder E-505C and Trefil® Powder E-506C by the company Dow Corning.

Preferably, the organic filler corresponds to polyamide powders.

The amount of fillers can vary to a large extent depending on the nature of the filler and also depending on the desired product and/or the desired effects; this amount is to be adjusted by those skilled in the art.

The filler(s) may be present in the composition in a content ranging from 0.01% to 50% by weight, in particular from 0.01% to 30% by weight, relative to the total weight of the composition, preferably ranging from 0.01% to 20% by weight.

More specifically, the filler(s) may be present in the composition in a content ranging from 1% to 50% by weight, relative to the total weight of the composition, and better still from 2% to 35% by weight.

When the composition according to the invention comprises mineral fillers and other fillers of organic type, they will be in said composition in a mineral fillers/organic fillers weight ratio of preferably greater than or equal to 1.

A subject of the present invention is also a composition, which can be used in a method according to the invention, comprising, in a physiologically acceptable medium, at least siloxane resins as defined above and at least one mineral filler as defined above, optionally also comprising at least one organic filler as defined above.

Other Components

The composition according to the invention may comprise one or more other components, and in particular components chosen from oils, nonionic surfactants, amphiphilic silicone elastomers, pasty compounds of nonanimal origin, fatty-phase thickening or gelling rheological agents (in particular with the exception of dimethicone crosspolymers), waxes (in particular with the exception of candelilla wax, ozokerite and silicone waxes), hydrophilic gelling agents, dyestuffs, in particular pigments or pearlescent agents optionally surface-treated with a hydrophobic agent, film-forming polymers, ionic surfactants (in particular with the exception of lauryl ether sulfate), fibers, and mixtures thereof.

In particular, the composition according to the invention may comprise one or more other components chosen from oils, nonionic surfactants, amphiphilic silicone elastomers, dyestuffs, fatty-phase thickening or gelling rheological agents (in particular with the exception of dimethicone crosspolymers), film-forming polymers, in particular lipophilic film-forming polymers, and mixtures thereof.

Silicone Elastomers

The compositions according to the invention may also comprise an amphiphilic silicone elastomer, preferably chosen from polyoxyalkylenated or polyglycerolated silicone elastomers.

As polyoxyalkylenated silicone elastomers, mention may be made of those described in U.S. Pat. No. 5,236,986, U.S. Pat. No. 5,412,004, U.S. Pat. No. 5,837,793 and U.S. Pat. No. 5,811,487.

As polyoxyalkylenated silicone elastomers, use may be made of:
those having the INCI name PEG-10 Dimethicone/Vinyl dimethicone crosspolymer: for instance those sold under the names KSG-21 and KSG-20 by Shin Etsu;
those having the INCI name Lauryl PEG-15 Dimethicone/Vinyl dimethicone Crosspolymer: for instance those sold under the names KSG-30 and KSG-31, KSG-32 (in isododecane), KSG-33 (in trioctanoin), KSG-210, KSG-310 (in a mineral oil), KSG-320 (in isododecane), KSG-330 and KSG-340 by the company Shin Etsu.

As polyglycerolated silicone elastomers, use may be made of:
those having the INCI name Dimethicone (and) Dimethicone/Polyglycerin-3 crosspolymer: for instance those sold under the name KSG-710 by Shin Etsu;
those having the INCI name Lauryl Dimethicone/Polyglycerin-3 crosspolymer: for instance those sold under the name KSG-840 (in squalene) by the company Shin Etsu.

These particular elastomers, when they are in combination with the resins according to the invention, can make it possible to improve the transfer-resistance and comfort (flexibility) properties of the compositions containing them.

Oils

The composition according to the invention may also comprise at least one oil.

The oil may be chosen from hydrocarbon-based oils, silicone oils and fluoro oils. These oils may be of animal, plant, mineral or synthetic origin.

The oil may be chosen from volatile oils and non-volatile oils, and mixtures thereof.

The term "hydrocarbon-based oil" is intended to mean oil formed essentially, or even consisting, of carbon and hydrogen atoms, and optionally of oxygen and nitrogen atoms, and containing no silicon or fluorine atom; it may contain ester, ether, amine and/or amide groups.

The term "silicone oil" is intended to mean oil containing at least one silicon atom, and in particular containing Si—O groups.

The term "fluoro" oil is intended to mean oil containing at least one fluorine atom.

The composition according to the invention may comprise at least one volatile oil.

The term "volatile oil" is intended to mean oil (or nonaqueous medium) capable of evaporating on contact with the skin in less than one hour, at ambient temperature and atmospheric pressure. The volatile oil is a volatile cosmetic oil which is liquid at ambient temperature and which has in particular a non-zero vapor pressure, at ambient temperature and atmospheric pressure, in particular which has a vapor pressure ranging from 0.13 Pa to 40 000 Pa ($10^{-3}$ to 300 mmHg), and preferably ranging from 1.3 Pa to 13 000 Pa (0.01 to 100 mmHg), and preferentially ranging from 1.3 Pa to 1300 Pa (0.01 to 10 mmHg).

In addition, the volatile oil generally has a boiling point, measured at atmospheric pressure, ranging from 150° C. to 260° C., and preferably ranging from 170° C. to 250° C.

The composition according to the invention may comprise a volatile hydrocarbon-based oil particularly chosen from hydrocarbon-based oils having a flash point ranging from 40° C. to 102° C., preferably ranging from 40° C. to 55° C., and preferentially ranging from 40° C. to 50° C.

As volatile hydrocarbon-based oil, mention may be made of volatile hydrocarbon-based oils containing from 8 to 16 carbon atoms and mixtures thereof, and in particular branched C8-C16 alkanes, for instance the C8-C16 isoalkanes (also known as isoparaffins), isododecane, isodecane and isohexadecane, and for example the oils sold under the trade names Isopars or Permethyls, branched C8-C16 esters, for instance isohexyl neopentanoate, and mixtures thereof. Preferably, the volatile hydrocarbon-based oil is chosen from volatile hydrocarbon-based oils containing from 8 to 16 carbon atoms and mixtures thereof, in particular from isododecane, isodecane and isohexadecane, and is in particular isododecane.

For good color staying power properties while retaining a matt deposit that is comfortable for foundation applications, volatile hydrocarbon-based solvents containing from 8 to 16 carbon atoms, in particular from 9 to 13 carbon atoms, will be preferred. As volatile C8 to C16 hydrocarbon-based solvents, mention may in particular be made of linear or branched alkanes, in particular branched alkanes, for instance the C8-C16 isoalkanes (also known as isoparaffins), isododecane, isodecane and isohexadecane, and for example the oils sold under the trade names Isopars or Permethyls, and mixtures thereof. Preferably, the volatile hydrocarbon-based solvent containing from 8 to 16 carbon atoms is chosen from isododecane, isodecane and isohexadecane, and mixtures thereof.

According to one particular embodiment, the volatile solvent is isododecane.

According to another particular embodiment, the volatile hydrocarbon-based solvent is a volatile linear alkane having a flash point included in the range of 70 to 120° C., and more particularly from 80 to 100° C., and which especially is approximately 89° C.

A volatile linear alkane suitable for the invention is liquid at ambient temperature (approximately 25° C.).

According to one embodiment, an alkane suitable for the invention may be a volatile linear alkane containing from 8 to 16 carbon atoms, in particular from 10 to 15 carbon atoms, and more particularly from 11 to 13 carbon atoms.

A volatile linear alkane suitable for the invention may be advantageously of plant origin. Such an alkane can be obtained, directly or in several steps, from a plant starting material, for instance an oil, a butter, a wax, etc.

By way of example of an alkane suitable for the invention, mention may be made of the alkanes described in patent application WO 2007/068371 from the company Cognis.

These alkanes are obtained from fatty alcohols, themselves obtained from coconut oil or palm oil.

By way of example of a linear alkane suitable for the invention, mention may be made of n-nonane (C9), n-decane (C10), n-undecane (C11), n-dodecane (C12), n-tridecane (C13), n-tetradecane (C14), n-pentadecane (C15), n-hexadecane (C16) and n-heptadecane (C17), and mixtures thereof, and in particular the mixture of n-undecane (C11) and n-tridecane (C13) sold under the reference Cetiol UT by the company Cognis.

According to one particular embodiment, a volatile linear alkane suitable for the invention may be chosen from n-nonane, n-undecane, n-dodecane, n-tridecane and n-heptadecane, and mixtures thereof.

More particularly, a volatile linear alkane suitable for the invention may be used in the form of an n-undecane/n-tridecane mixture.

Preferably, in such a mixture, the n-undecane:n-tridecane weight ratio may be 50:50 to 90:10, preferably ranging from 60:40 to 80:20, preferably ranging from 65:35 to 75:25.

In particular, a composition according to the invention may comprise an n-undecane:n-tridecane mixture in a 70:30 weight ratio. Such a mixture is sold under the name Cetiol UT by the company Cognis.

For skin makeup products, in particular foundations and lipsticks, volatile linear hydrocarbon-based oils having from 8 to 16 carbon atoms will advantageously be used.

As volatile silicone oils, mention may be made of linear or cyclic silicones containing from 2 to 7 silicon atoms, these silicones optionally comprising alkyl or alkoxy groups containing from 1 to 10 carbon atoms. As volatile silicone oils that can be used in the invention, mention may in particular be made of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane and decamethyltetrasiloxane, and mixtures thereof.

The volatile oil may be present in the composition according to the invention in a content ranging from 0.1% to 90% by weight, relative to the total weight of the composition, preferably ranging from 1% to 70% by weight, and preferentially ranging from 5% to 50% by weight.

The composition according to the invention may comprise at least one non-volatile oil.

The term "non-volatile oil" is intended to mean oil which remains on the keratin materials at ambient temperature and atmospheric pressure for at least several hours and which has in particular a vapor pressure of less than $10^{-3}$ mmHg (0.13 Pa). A non-volatile oil can also be defined as having a rate of evaporation such that, under the conditions defined above, the amount evaporated after 30 minutes is less than 0.07 mg/cm$^2$.

As a non-volatile hydrocarbon-based oil, use may be made of liquid paraffin (or petroleum jelly), squalane, hydrogenated polyisobutylene (Parleam oil), perhydrosqualene, mink oil, turtle oil, soybean oil, sweet almond oil, beauty-leaf oil, palm oil, grapeseed oil, sesame oil, corn oil, arara oil, rapeseed oil, sunflower oil, cottonseed oil, apricot oil, castor oil, avocado oil, jojoba oil, olive oil or cereal germ oil; lanolic acid, oleic acid, lauric acid or stearic acid esters; fatty esters, in particular of C12-C36, such as isopropyl myristate, isopropyl palmitate, butyl stearate, hexyl laurate, diisopropyl adipate, 2-ethylhexyl palmitate, 2-hexyldecyl laurate, 2-octyldecyl palmitate, 2-octyldodecyl myristate or lactate, bis(2-ethylhexyl) succinate, diisostearyl malate, glyceryl or diglyceryl triisostearate; behenic acid, oleic acid, linoleic acid, linolenic acid or isostearic acid; higher fatty alcohols, in particular of C16-C22, such as cetanol, oleyl alcohol, linoleyl alcohol, linolenyl alcohol, isostearyl alcohol or octyldodecanol; and mixtures thereof.

In particular, in order to obtain a makeup which renders the complexion matt while at the same time retaining comfortable use, both during application of makeup and afterwards, use will be made of the non-volatile C6-C22 hydrocarbon-based oils that can be chosen from:

carbonates, of following formula (I): R1-O—C(=O)—O—R'1, with R1 and R'1, which may be identical or different, representing a linear or branched, saturated or unsaturated (preferably saturated), C4 to C12, and preferentially C5 to C10, alkyl chain optionally having at least one saturated or unsaturated, preferably saturated, ring;

it being possible for these oils of formula (I) to be dicaprylyl carbonate, sold under the name Cetiol CC® by the company Cognis, bis(2-ethylhexyl) carbonate, sold under the name Tegosoft DEC® by the company Goldschmidt, diisobutyryl carbonate; dineopentyl carbonate; dipentyl carbonate; dineoheptyl carbonate; diheptyl carbonate; diisononyl carbonate; or dinonyl carbonate;

monoesters, of formula (II): R2-O—C(=O)—R'2, with R2 and R'2, which may be identical or different, representing a linear or branched, saturated or unsaturated (preferably saturated), C4 to C12, and preferentially C5 to C10, alkyl chain optionally having at least one saturated or unsaturated, preferably saturated, ring;

it being possible for these oils of formula (II) to be 2-ethylhexyl isobutyrate, 2-ethylhexyl butyrate, caprylyl butyrate, isononyl isobutyrate, 2-ethylhexyl hexanoate, isononyl hexanoate, neopentyl hexanoate, caprylyl heptanoate, octyl octanoate, sold under the name Dragoxat EH® by the company Symrise, or isononyl isononanoate;

diesters, of following formula (III): R3-O—C(=O)—R'3-C(=O)—O—R"3, with R3 and R"3, which may be identical or different, representing a linear or branched, saturated or unsaturated (preferably saturated), C4 to C12, preferably C5 to C10, alkyl chain optionally having at least one saturated or unsaturated, preferably saturated, ring, and R'3 representing a saturated or unsaturated, C1 to C4, preferably C2 to C4, alkylene chain, for instance an alkylene chain derived from succinate (in this case, R'3 is a saturated C2 alkylene chain), maleate (in this case, R'3 is an unsaturated C2 alkylene chain), glutarate (in this case, R'3 is a saturated C3 alkylene chain) or adipate (in this case, R'3 is a saturated C4 alkylene chain); in particular, R3 and R"3 are chosen from isobutyl, pentyl, neopentyl, hexyl, heptyl, neoheptyl, 2-ethylhexyl, octyl, nonyl and isononyl; mention may preferentially be made of dicaprylyl maleate, in particular sold by the company Alzo; or bis(2-ethylhexyl) succinate;

ethers, of following formula (IV): R4-O—R4', with R4 and R4', which may be identical or different, representing a linear or branched, saturated or unsaturated (preferably saturated), C4 to C12, and preferentially C5 to C10, alkyl chain optionally having at least one saturated or unsaturated, preferably saturated, ring; in particular, R4 and R4' are chosen from isobutyl, pentyl, neopentyl, hexyl, heptyl, neoheptyl, 2-ethylhexyl, octyl, nonyl and isononyl; among the compounds of formula (IV) mention may preferentially be made of dicaprylyl ether, sold under the name Cetiol OE® by the company Cognis;

alkyl triesters, of formula (V): R5-O—C(O)—CH$_2$—CH[—O—C(O)—R'5]-CH$_2$—O—C(O)—R"5, with R5, R'5 and R"5, which may be identical or different, representing a linear or branched, saturated or unsaturated (preferably saturated), C4-C10, preferably C5-C8, alkyl chain; in particular, R5, R'5 and R"5 are identical; preferably R5, R'5 and R"5 (in particular identical) are alkyl radicals of the following fatty acids: caprylic acid, 2-ethylhexanoic acid, neopentanoic acid or neoheptanoic acid; as compound of formula (V), mention may preferentially be made of caprylic/capric triglyceride, sold in particular under the name Myritol 318® by the company Cognis;

and mixtures thereof.

The non-volatile C6-C22 hydrocarbon-based oil advantageously used in said makeup and/or care compositions intended to render the complexion matt is dicaprylyl carbonate, in particular sold under the name Cetiol CC by the company Cognis.

Advantageously, when the composition is intended for making up and/or caring for the lips, and comprises a non-volatile oil, this oil is chosen from phenyl silicone oils. Such an oil is also known as a phenyl silicone.

The term "phenyl silicone" is intended to mean an organopolysiloxane substituted with at least one phenyl group.

The phenyl silicone is preferably non-volatile. The term "non-volatile" is intended to mean an oil of which the vapor pressure at ambient temperature and atmospheric pressure is non-zero and less than 0.13 Pa.

Preferably, the weight-average molecular weight of the phenyl silicone oil is between 500 and 10 000 g/mol.

The silicone oil may be chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

The silicone oil may correspond to the formula:

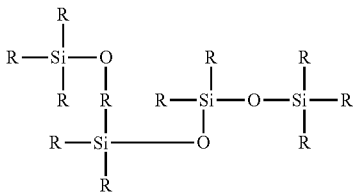

in which the R groups represent, independently of one another, a methyl or a phenyl. Preferably, in this formula, the silicone oil comprises at least three phenyl groups, for example at least four, at least five or at least six.

According to another embodiment, the silicone oil corresponds to the formula:

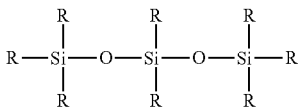

in which the R groups represent, independently or one another, a methyl or a phenyl. Preferably, in this formula, said organopolysiloxane comprises at least three phenyl groups, for example at least four or at least five.

Mixtures of the phenyl organopolysiloxanes described above can be used.

By way of example, mention may be made of mixtures of triphenyl-, tetraphenyl- or pentaphenylorganopolysiloxane.

According to another embodiment, the silicone oil corresponds to the formula:

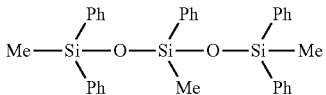

in which Me represents methyl and Ph represents phenyl. Such a phenyl silicone is in particular produced by Dow Corning under the reference Dow Corning 555 Cosmetic Fluid (INCI name: trimethyl pentaphenyl trisiloxane). The reference Dow Corning 554 Cosmetic Fluid can also be used.

According to another embodiment, the silicone oil corresponds to the formula:

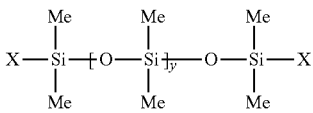

in which Me represents methyl, y is between 1 and 1000, and X represents —CH$_2$—CH(CH$_3$)(Ph).

According to another embodiment, the silicone oil corresponds to the formula:

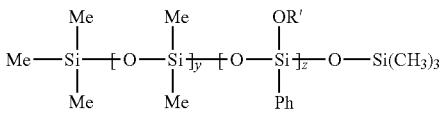

in which —OR' represents —O—SiMe$_3$, y is between 1 and 1000 and z is between 1 and 1000.

The phenyl silicone oil can be chosen from the phenyl silicones of following formula (VI):

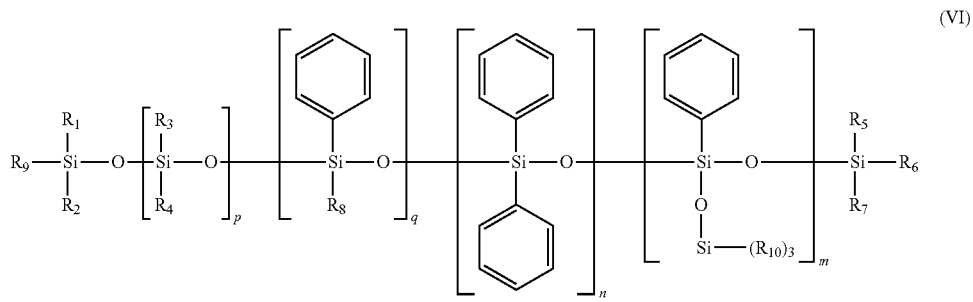

(VI)

in which:
- $R_1$ to $R_{10}$, independently of one another, are saturated or unsaturated, linear, cyclic or branched, C1-C30 hydrocarbon-based radicals,
- m, n, p and q are, independently of one another, integers between 0 and 900, with the proviso that the sum 'm+n+q' is other than 0.

Preferably, the sum 'm+n+q' is between 1 and 100. Preferably, the sum 'm+n+p+q' is between 1 and 900, even better still between 1 and 800. Preferably, q is equal to 0.

The phenyl silicone oil can be chosen from the phenyl silicones of following formula (VII):

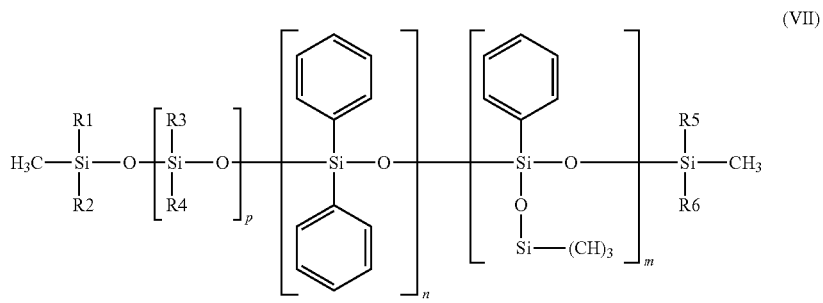

(VII)

in which:
- R1 to R6, independently of one another, are saturated or unsaturated, linear, cyclic or branched, C1-C30 hydrocarbon-based radicals,
- m, n and p are, independently of one another, integers between 0 and 100, with the proviso that the sum 'n+m' is between 1 and 100.

Preferably, R1 to R6, independently of one another, represent a linear or branched, saturated, C1-C30, in particular C1-12, hydrocarbon-based radical, and in particular a methyl, ethyl, propyl or butyl radical.

In particular, R1 to R6 may be identical, and in addition may be a methyl radical.

Preferably, it is possible to have m=1 or 2 or 3, and/or n=0 and/or p=0 or 1, in formula (VII).

It is possible to use a phenyl silicone oil of formula (VI) having a viscosity at 25° C. of between 5 and 1500 mm²/s (i.e. 5 to 1500 cSt), preferably having a viscosity between 5 and 1000 mm²/s (i.e. 5 to 1000 cSt).

As phenyl silicone oil of formula (VII), use may in particular be made of phenyl trimethicones, such as DC556 from Dow Corning (22.5 cSt), the Silbione 70663V30 oil from Rhone Poulenc (28 cSt), or diphenyl dimethicones, such as the Belsil oils, in particular Belsil PDM1000 (1000 cSt), Belsil PDM 200 (200 cSt) and Belsil PDM 20 (20 cSt) from Wacker. The values between parentheses represent the viscosities at 25° C.

The non-volatile silicone oil may be chosen from the silicones of formula:

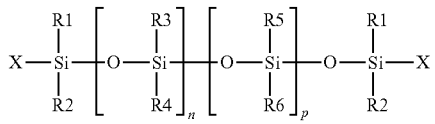

in which:
R1, R2, R5 and R6 are, together or separately, an alkyl radical containing 1 to 6 carbon atoms,
R3 and R4 are, together or separately, an alkyl radical containing from 1 to 6 carbon atoms, or an aryl radical,
X is an alkyl radical containing from 1 to 6 carbon atoms, a hydroxyl radical or a vinyl radical, n and p being chosen so as to confer on the oil a weight-average molecular weight of less than 200 000 g/mol, preferably less than 150 000 g/mol and more preferably less than 100 000 g/mol.

The non-volatile oil may be present in a content ranging from 0.1% to 70% by weight, relative to the total weight of the non-volatile liquid fatty phase, preferably ranging from 0.5% to 60% by weight, and preferentially ranging from 1% to 50% by weight.

For skin makeup products, in particular foundations and lipsticks, volatile or non-volatile linear silicone oils will advantageously be used. The combination of the resins according to the invention and of a linear silicone oil can in particular make it possible to improve the transfer resistance.

For skin makeup products, in particular lipsticks, phenyl silicone oils will advantageously be used. The combination of the resins according to the invention and of a phenyl silicone oil can in particular make it possible to improve the gloss and the comfort and to reduce the tacky sensation.

Nonionic Surfactants

The composition according to the invention may comprise at least one nonionic surfactant.

In particular, use may be made of an emulsifier having, at 25° C., an HLB balance (hydrophilic-lipophilic balance), within the meaning of Griffin, specific for the composition that it is intended to obtain.

The HLB value according to Griffin is defined in J. Soc. Cosm. Chem. 1954 (volume 5), pages 249-256.

Reference may be made to the document "Encyclopedia of Chemical Technology, KIRK-OTHMER", volume 22, p. 333-432, 3rd edition, 1979, Wiley, for the definition of the properties and of the (emulsifying) functions of surfactants, in particular p. 347-377 of this reference, for nonionic surfactants.

The nonionic surfactants preferentially used in the composition according to the invention are chosen from:

a) nonionic surfactants with an HLB greater than or equal to 8 at 25° C., used alone or as a mixture; mention may in particular be made of:

saccharide esters and ethers, such as the mixture of cetylstearyl glucoside and cetyl and stearyl alcohols, for instance Montanov 68 from Seppic;

oxyethylenated and/or oxypropylenated ethers (that may comprise from 1 to 150 oxyethylene and/or oxypropylene groups) of glycerol;

oxyethylenated and/or oxypropylenated ethers (that may comprise from 1 to 150 oxyethylene and/or oxypropylene groups) of fatty alcohols (in particular of C8-C24, and preferably C12-C18, alcohol), such as oxyethylenated cetearyl alcohol ether comprising 30 oxyethylene groups (CTFA name Ceteareth-30), oxyethylenated stearyl alcohol ether comprising 20 oxyethylene groups (CTFA name Steareth-20) and the oxyethylenated ether of the mixture of C12-C15 fatty alcohols comprising 7 oxyethylene groups (CTFA name C12-15 Pareth-7) sold under the name Neodol 25-7® by Shell Chemicals;

fatty acid esters (in particular of a C8-C24 and preferably C16-C22 acid) of polyethylene glycol (which may comprise from 1 to 150 ethylene glycol units), such as PEG-50 stearate and PEG-40 monostearate sold under the name Myrj 52P® by the company ICI Uniquema;

fatty acid esters (in particular of a C8-C24 and preferably C16-C22 acid) of oxyethylenated and/or oxypropylenated glyceryl ethers (which may comprise from 1 to 150 oxyethylene and/or oxypropylene groups), for instance PEG-200 glyceryl monostearate sold under the name Simulsol 220 ™® by the company SEPPIC; glyceryl stearate polyethoxylated with 30 ethylene oxide groups, for instance the product Tagat S® sold by the company Goldschmidt, glyceryl oleate polyethoxylated with 30 ethylene oxide groups, for instance the product Tagat O® sold by the company Goldschmidt, glyceryl cocoate polyethoxylated with 30 ethylene oxide groups, for instance the product Varionic LI 13® sold by the company Sherex, glyceryl isostearate polyethoxylated with 30 ethylene oxide groups, for instance the product Tagat L® sold by the company Goldschmidt, and glyceryl laurate polyethoxylated with 30 ethylene oxide groups, for instance the product Tagat I® from the company Goldschmidt;

fatty acid esters (in particular of a C8-C24 and preferably C16-C22 acid) of oxyethylenated and/or oxypropylenated sorbitol ethers (which may comprise from 1 to 150 oxyethylene and/or oxypropylene groups), for instance polysorbate 20 sold under the name Tween 20® by the company Croda, polysorbate 60 sold under the name Tween 60® by the company Croda;

dimethicone copolyol, such as the product sold under the name Q2-5220® by the company Dow Corning;

dimethicone copolyol benzoate (Finsolv SLB 101® and 201® from the company Fintex);

copolymers of propylene oxide and of ethylene oxide, also known as EO/PO polycondensates;

and mixtures thereof.

The EO/PO polycondensates are more particularly copolymers consisting of polyethylene glycol and polypropylene glycol blocks, for instance polyethylene glycol/polypropylene glycol/polyethylene glycol triblock polycondensates. These triblock polycondensates have, for example, the following chemical structure:

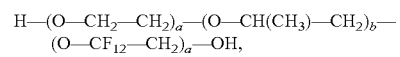

in which formula a ranges from 2 to 120, and b ranges from 1 to 100.

The EO/PO polycondensate preferably has a weight-average molecular weight ranging from 1000 to 15 000, and better still ranging from 2000 to 13 000. Advantageously, said ED/PO polycondensate has a cloud point, at 10 g/l in distilled water, of greater than or equal to 20° C., preferably greater than or equal to 60° C. The cloud point is measured according to standard ISO 1065. As EO/PO polycondensate that can be used according to the invention, mention may be made of the polyethylene glycol/polypropylene glycol/polyethylene glycol triblock polycondensates sold under the name Synperonic®, for instance Synperonic PE/L44® and Synperonic PE/F127®, by the company ICI;

b) nonionic surfactants with an HLB of less than 8 at 25° C., optionally combined with one or more nonionic surfactants with an HLB of greater than 8 at 25° C., as mentioned above, such as:

saccharide esters and ethers, such as sucrose stearate, sucrose cocoate and sorbitan stearate, and mixtures thereof, for instance Arlatone 2121® sold by the company ICI;

oxyethylenated and/or oxypropylenated ethers (which may comprise from 1 to 150 oxyethylene and/or oxypropylene groups) of fatty alcohols (in particular of a C8-C24 and preferably C12-C18 alcohol), such as oxyethylenated stearyl alcohol ether comprising 2 oxyethylene groups (CTFA name Steareth-2);

fatty acid esters (in particular of a C8-C24 and preferably C16-C22 acid) of a polyol, in particular of glycerol or of sorbitol, such as glyceryl stearate, glyceryl stearate such as the product sold under the name Tegin M® by the company Goldschmidt, glyceryl laurate such as the product sold under the name Imwitor 312® by the company Huls, polyglyceryl-2 stearate, sorbitan tristearate or glyceryl ricinoleate;

lecithins, such as soybean lecithins (for instance Emulmetik 100 J from Cargill, or Biophilic H from Lucas Meyer);

the mixture of cyclomethicone/dimethicone copolyol sold under the name Q2-3225C® by the company Dow Corning.

The nonionic surfactant may also be chosen from a C8-C22 alkyl dimethicone copolyol, i.e. an oxypropylenated and/or oxyethylenated polymethyl (C8-C22) alkyldimethylmethylsiloxane.

The C8-C22 alkyl dimethicone copolyol is advantageously a compound of formula (I) below:

$$(CH_3)_3Si-O \left[ \begin{array}{c} CH_3 \\ | \\ Si-O \\ | \\ (CH_2)_p \\ | \\ CH_3 \end{array} \right]_o \left[ \begin{array}{c} CH_3 \\ | \\ Si-O \\ | \\ (CH_2)_q \\ | \\ O \\ | \\ PE \end{array} \right]_m \left[ \begin{array}{c} CH_3 \\ | \\ Si-O \\ | \\ CH_3 \end{array} \right]_n Si(CH_3)_3 \quad (I)$$

in which:
PE represents $(-C_2H_4O)_x-(C_3H_6O)_y-R$, R being chosen from a hydrogen atom and an alkyl radical containing from 1 to 4 carbon atoms, x ranging from 0 to 100 and y ranging from 0 to 80, and x and y not being simultaneously 0
m ranging from 1 to 40
n ranging from 10 to 200
o ranging from 1 to 100
p ranging from 7 to 21
q ranging from 0 to 4
and preferably:
R=H; m=1 to 10; n=10 to 100; o=1 to 30; p=15 and q=3.

As C8-C22 alkyl dimethicone copolyol, mention may be made of cetyl dimethicone copolyol, for instance the product sold under the name Abil EM-90 by the company Goldschmidt.

According to one particular embodiment intended for formulating stable emulsions, having a low viscosity allowing easy application, while at the same time conferring, on the makeup product, staying power of the makeup product over time once applied, use will advantageously be made of at least one nonionic silicone surfactant, optionally combined with at least one hydrocarbon-based surfactant and optionally also at least one wax.

As nonionic silicone surfactant, mention may, for example, be made of:
a) polydialkyl silicones comprising polyoxyalkylenated (polyoxyethylenated (or PEO) and/or polyoxypropylenated (or PPO)) hydrophilic side and/or end groups. In addition, these silicone surfactants preferably comprise linear or branched C1 to C20 alkyl side groups, preferably linear alkyl groups, such as lauryl or cetyl. These surfactants may also bear organosiloxane side groups.

In particular, in this first category, mention may be made of:
polymethylsiloxanes comprising PEO side groups, such as in particular KF-6011, KF-6012, KF-6013, KF-6015, KF-6016 and KF-6017 from the company Shin Etsu;
polydimethylsiloxanes comprising PEO side groups and comprising alkyl side groups, such as in particular cetyl PEG-PPG 10/1 dimethicone, sold under the name Abil EM90 by the company Evonik Goldschmidt;
branched polydimethylsiloxanes comprising PEO side groups, such as in particular PEG-9 polydimethylsiloxyethyl dimethicone, sold under the name KF-6028 by the company Shin Etsu;
branched polydimethylsiloxanes comprising alkyl side groups, such as in particular lauryl PEG-9 polydimethylsiloxyethyl dimethicone, sold under the name KF-6038 by the company Shin Etsu;
b) polydialkyl silicones comprising polyglycerolated or glycerolated side groups. These silicone surfactants also preferably comprise linear or branched C1 to C20 alkyl side groups, and preferably also linear alkyl groups, such as lauryl or cetyl. Likewise, these glycerolated silicone surfactants may also bear organosiloxane side groups.

In particular, in this category, mention may be made of:
polydimethylsiloxanes comprising polyglycerolated side groups, such as polyglyceryl-3 disiloxane dimethicone, sold under the name KF-6100 by the company Shin Etsu;
branched polydimethylsiloxanes comprising polyglycerolated side groups, such as polyglyceryl-3 polydimethylsiloxyethyl dimethicone, sold under the name KF-6104 by the company Shin Etsu;
branched polydimethylsiloxanes comprising polyglycerolated side groups and alkyl side groups, such as lauryl polyglyceryl-3 polydimethylsiloxyethyl dimethicone, sold under the name KF-6105 by the company Shin Etsu.

Among the nonionic silicone surfactants, cetyl PEG/PPG-10/1 dimethicone, sold under the name Abil EM90 by the company Evonik Goldschmidt, is preferred.

The nonionic silicone surfactant is advantageously in combination with at least one nonionic organic surfactant.

As nonionic organic surfactant, mention may be made of fatty acid esters of polyols, for instance sorbitol or glycerol mono-, di-, tri- or sesquioleates or stearates, or glycerol or polyethylene glycol laurates; fatty acid esters of polyethylene glycol (polyethylene glycol monostearate or monolaurate); polyoxyethylenated fatty acid esters (stearate, oleate) of sorbitol; polyoxyethylenated alkyl (lauryl, cetyl, stearyl, octyl) ethers.

Among the nonionic organic surfactants, the following are preferred:
polyglycerolated fatty acid esters comprising at least three glycerol ether units, such as polyglyceryl-3;
polyoxyalkylenated (polyoxyethylenated and/or polyoxypropylenated) fatty acid esters, preferably comprising at least three oxyethylene groups;
fatty alcohol ethers of polyglycerols with at least 3 glyceryl ether units;
fatty alcohol ethers of polyoxyalkylene (PEO and/or PEO/PPO) with at least 3 PEO groups.

Among the nonionic organic surfactants, the polyglyceryl-4 isostearate sold under the name Isolan G1340 by the company Evonik Goldschmidt is preferred.

At least one wax may advantageously be used in combination with the nonionic silicone surfactant and the nonionic organic surfactant.

Among the waxes, the mixture of ethylene glycol acetyl stearate/glyceryl tristearate, in particular sold under the name Unitwix by the company United Guardian, is preferred.

Fatty-Phase Thickening or Gelling Rheological Agent

The composition according to the invention may also comprise a fatty-phase thickening or gelling rheological agent.

The expression "fatty-phase thickening or gelling rheological agent" is intended to mean a compound capable of increasing the viscosity of the fatty phase of the composition. The fatty-phase thickening or gelling rheological agent makes it possible in particular to obtain a composition that can have a texture ranging from fluid to solid textures.

Preferably, the fatty-phase thickening or gelling rheological agents are chosen from crystalline polymers, mineral lipophilic structuring agents, lipophilic polyamides, lipophilic polyureas and polyurethanes, silicone polymers comprising, as appropriate, at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups and combinations thereof, organogelling agents, block polymers, cholesterol-based liquid crystal agents, dimethicone/vinyl dimethicone copolymers, and vinyl dimethicone/alkyl dimethicone copolymers, such as vinyl dimethicone/lauryl dimethicone copolymers.

The fatty-phase thickening or gelling rheological agent may be chosen from:
- crystalline polymers, preferably chosen from semi-crystalline polymers, fatty acid esters of dextrin, hydrophobically modified polysaccharides, crystalline olefin copolymers and crystalline polycondensates;
- mineral lipophilic structuring agents, for instance lipophilic clays and hydrophobic silicas, for instance hydrophobically-treated fumed silica,
- lipophilic polyamide-type polymers,
- lipophilic polyureas and polyurethanes,
- silicone polymers comprising, where appropriate, at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups and combinations thereof, preferably amide groups,
- organogelling agents;
- block polymers;
- cholesterol-based liquid crystal agents;
- silicone elastomers;
- and mixtures thereof.

Preferably, the fatty-phase rheological agent is chosen from semi-crystalline polymers, block polymers, lipophilic polyamide-type polymers, and silicone polymers comprising at least one hydrocarbon-based unit comprising two groups capable of establishing hydrogen interactions, chosen from amide groups, mineral lipophilic structuring agents, in particular lipophilic clays and hydrophobic silicas, and silicone elastomers.

It is specified that, according to the invention, in the case of the combinations of a fatty-phase rheological agent with an oil, the term "oil" is intended to mean a fatty substance that is liquid at ambient temperature. The oils may be those described above.

Mineral Lipophilic Structuring Agents

The fatty-phase thickening or gelling rheological agent may be a mineral lipophilic structuring agent.

Mention may in particular be made of lipophilic clays, for instance optionally modified clays, such as hectorites modified with a $C_{10}$ to $C_{22}$ ammonium chloride, for instance hectorite modified with distearyldimethylammonium chloride.

Clays are silicates containing a cation which can be chosen from calcium, magnesium, aluminum, sodium, potassium and lithium cations, and mixtures thereof.

By way of examples of such products, mention may be made of clays of the smectite family, such as montmorillonites, hectorites, bentonites, beidellites or saponites, and also of the vermiculite, stevensite and chlorite family. These clays may be of natural or synthetic origin.

The clay may be chosen from montmorrillonite, bentonite, hectorite, attapulgite and sepiolite, and mixtures thereof. The clay is preferably a bentonite or a hectorite.

Organophilic clays are clays modified with a chemical compound chosen from quaternary amines, tertiary amines, amine acetates, imidazolines, amine soaps, fatty sulfates, alkyl aryl sulfonates and amine oxides, and mixtures thereof.

As organophilic clays, mention may be made of quaternium-18 bentonites such as those sold under the names Bentone 3, Bentone 38 and Bentone 38V by the company Elementis, Tixogel VP by the company United Catalyst, Claytone 34, Claytone 40 and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; quaternium-18/benzalkonium bentonites such as those sold under the names Claytone HT and Claytone PS by the company Southern Clay.

According to one preferred embodiment, the thickening agent is chosen from organophilic modified clays, such as hectorite modified with benzyldimethylammonium stearate.

Mention may also be made of hydrophobic silicas, for instance fumed silica optionally subjected to a hydrophobic surface treatment, the particle size of which is less than 1 µm. It is in fact possible to chemically modify the surface of the silica, by chemical reaction generating a reduced number of silanol groups present at the surface of the silica. It is in particular possible to substitute silanol groups with hydrophobic groups: a hydrophobic silica is then obtained. The hydrophobic groups may be:
- trimethylsiloxyl groups, which are in particular obtained by treatment of fumed silica in the presence of hexamethyldisilazane. Silicas thus treated are known as "silica silylate" according to the CTFA ($6^{th}$ edition, 1995). They are sold, for example, under the references Aerosil R812® by the company Degussa, and Cab-O-Sil TS-530® by the company Cabot;
- dimethylsilyloxyl or polydimethylsiloxane groups, which are obtained in particular by a treatment of fumed silica in the presence of polydimethylsiloxane or of dimethyldichlorosilane. Silicas thus treated are known as "silica dimethyl silylate" according to the CTFA ($6^{th}$ edition, 1995). They are, for example, sold under the references Aerosil R972® and Aerosil R974® by the company Degussa, and Cab-O-Sil TS-610® and Cab-O-Sil TS-720® by the company Cabot.

The hydrophobic fumed silica preferably has a particle size that may be nanometric to micrometric, for example ranging from about 5 to 200 nm.

Lipophilic Polyamide Polymers

For the purpose of the invention, the term "polymer" is intended to mean a compound having at least 2 repeating units, preferably at least 3 repeating units and better still 10 repeating units.

As preferred lipophilic structuring polyamide polymers that may be used in the invention, mention may be made of polyamides branched with pendant fatty chains and/or terminal fatty chains containing from 12 to 120 carbon atoms and in particular from 12 to 68 carbon atoms, the terminal fatty chains being bonded to the polyamide backbone via ester groups. These polymers are more especially those described in document U.S. Pat. No. 5,783,657 from the company Union Camp. In particular, mention may be made of the polymers of which the INCI name is "ethylenediamine/stearyl dimer dilinoleate copolymer" and "ethylenediamine/stearyl dimer tallate copolymer".

By way of examples of structuring polymers that can be used in the composition according to the invention, mention may be made of the commercial products sold by the company Bush Boake Allen under the names Uniclear 80, Uniclear 100, Uniclear 80 V, Uniclear 100 V and Uniclear 100 VG. They are sold, respectively, in the form of a gel at 80% (with respect to active material) in a mineral oil and at 100% (with respect to active material). They have a softening point of from 88 to 94° C. These commercial products are a mixture of copolymer of a $C_{36}$ diacid coupled with ethylenediamine, having an average molecular weight of approximately 6000. The remaining acid end groups are, in addition, esterified with cetyl alcohol, stearyl alcohol or mixtures thereof (also known as cetylstearyl alcohol).

Lipophilic Polyurea or Polyurethane Polymers

As fatty-phase rheological agent, mention may also be made of polyurethanes and polyureas that are soluble or dispersible in hydrocarbon-based oil(s), and which comprise:
- at least two urethane groups, or at least two urea groups, or at least one urethane group and one urea group in the chain,
- at least one hydrocarbon-based long-chain, preferably branched, aliphatic polyester or hydrocarbon-based graft or block.

The term "hydrocarbon-based long chain" is intended to mean a linear or branched hydrocarbon-based chain containing at least 8 carbon atoms and preferably 10 to 500 carbon atoms.

Lipophilic Silicone Polymers:

The silicone polymeric lipophilic structuring agents are, for example, polymers of the polyorganosiloxane type, for instance those described in documents U.S. Pat. No. 5,874,069, U.S. Pat. No. 5,919,441, U.S. Pat. No. 6,051,216 and U.S. Pat. No. 5,981,680. According to the invention, the polymers used as structuring agent can belong to the following two families:

1) polyorganosiloxanes comprising at least two groups capable of establishing hydrogen interactions, these two groups being located in the polymer chain, and/or
2) polyorganosiloxanes comprising at least two groups capable of establishing hydrogen interactions, these two groups being located on grafts or branches.

The groups capable of establishing hydrogen interactions can be chosen from ester, amide, sulfonamide, carbamate, thiocarbamate, urea, urethane, thiourea, oxamido, guanidino and biguanidino groups and combinations thereof.

According to a first variant, the silicone polymers are polyorganosiloxanes as defined above in which the units capable of establishing hydrogen interactions are located in the polymer chain.

According to one variant of the invention, it is also possible to use a polymer comprising, in addition, at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups and combinations thereof.

These copolymers may be block polymers, sequenced or grafted polymers.

By way of example of a silicone polymer that can be used, mention may be made of one of the silicone polyamides obtained in accordance with examples 1 to 3 of document U.S. Pat. No. 5,981,680.

According to one embodiment variant of the invention, the polymer is made up of a homopolymer or copolymer comprising urethane or urea groups. These polymers are described in detail in application WO 2003/106614 published on Dec. 24, 2003, the content of which is incorporated into the present application by way of reference.

The polymers and copolymers used in the composition of the invention advantageously have a solid-liquid transition temperature of 45° C. to 190° C. Preferably, they have a solid-liquid transition temperature ranging from 70° C. to 130° C. and better still from 80° C. to 105° C.

Organogelling Agents:

The oily structuring agent may also be chosen from non-polymeric molecular organic gelling agents, also known as organogelling agents, which are compounds whose molecules are capable of establishing between themselves physical interactions leading to self-aggregation of the molecules with formation of a supramolecular 3D network that is responsible for the gelation of the oil(s) (also known as the liquid fatty phase).

The supramolecular network may result from the formation of a network of fibrils (caused by the stacking or aggregation of organogelling molecules), which immobilizes the molecules of the liquid fatty phase.

The ability to form this network of fibrils, and thus to gel, depends on the nature (or chemical class) of the organogelling agent, on the nature of the substituents borne by its molecules for a given chemical class, and on the nature of the liquid fatty phase.

The physical interactions are of diverse nature but exclude co-crystallization. These physical interactions are in particular interactions of self-complementary hydrogen interaction type, π interactions between unsaturated rings, dipolar interactions, coordination bonds with organometallic derivatives, and combinations thereof. In general, each molecule of an organogelling agent can establish several types of physical interaction with a neighboring molecule. Thus, advantageously, the molecules of the organogelling agents according to the invention comprise at least one group capable of establishing hydrogen bonds and better still at least two groups capable of establishing hydrogen bonds, at least one aromatic ring and better still at least two aromatic rings, at least one or more ethylenically unsaturated bonds and/or at least one or more asymmetric carbons. Preferably, the groups capable of forming hydrogen bonds are chosen from hydroxyl, carbonyl, amine, carboxylic acid, amide, urea and benzyl groups, and combinations thereof.

The organogelling agent(s) according to the invention is (are) soluble in the liquid fatty phase after heating to obtain a transparent uniform liquid phase. They may be solid or liquid at room temperature and atmospheric pressure.

The molecular organogelling agent(s) that may be used in the composition according to the invention is (are) especially those described in the document "Specialist Surfactants" edited by D. Robb, 1997, pp. 209-263, Chapter 8 by P. Terech, European patent applications EP-A-1 068 854 and EP-A-1 086 945, or alternatively in patent application WO-A-02/47031.

Mention may be made especially, among these organogelling agents, of amides of carboxylic acids, in particular of tricarboxylic acids, for instance cyclohexanetricarboxamides (see European patent application EP-A-1 068 854), diamides with hydrocarbon-based chains each containing from 1 to 22 carbon atoms, for example from 6 to 18 carbon atoms, said chains being unsubstituted or substituted with at least one substituent chosen from ester, urea and fluoro groups (see patent application EP-A-1 086 945) and especially diamides resulting from the reaction of diaminocyclohexane, in particular diaminocyclohexane in trans form, and of an acid chloride, for instance N,N'-bis-(dodecanoyl)-1,2-diaminocyclohexane, N-acylamino acid amides, for instance the diamides resulting from the action of an N-acylamino acid with amines containing from 1 to 22 carbon atoms, for instance those described in document WO-93/23008 and especially N-acylglutamic acid amides in which the acyl group represents a $C_8$ to $C_{22}$ alkyl chain, such as N-lauroyl-L-glutamic acid dibutylamide, manufactured or sold by the company Ajinomoto under the name GP-1, and mixtures thereof.

It is also possible to use, as organogelling agents, compounds of bis-urea type having the following general formula:

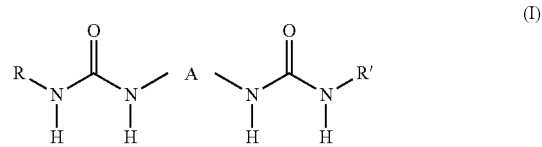

(I)

in which:
A is a group of formula (II):

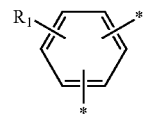

with $R_1$ being a linear or branched $C_1$-$C_4$ alkyl radical, and the *s symbolizing the points of attachment of the group A to each of the two nitrogen atoms of the rest of the compound of general formula (I), and R and R', which may be identical or different, are chosen from:

i) the radicals of formula (III):

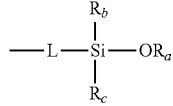
(III)

in which:

L is a single bond or a divalent carbon-based radical, especially a linear, branched and/or cyclic, saturated or unsaturated hydrocarbon-based radical (alkylene), containing 1 to 18 carbon atoms, and possibly comprising 1 to 4 heteroatoms chosen from N, O and S;

$R_a$ is:

a) a carbon-based radical, especially a linear, branched and/or cyclic, saturated or unsaturated hydrocarbon-based radical (alkyl), containing 1 to 18 carbon atoms, and possibly comprising 1 to 8 heteroatoms chosen from N, O, Si and S; or b) a silicone radical of formula:

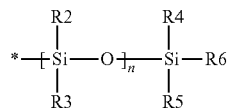

with n being between 0 and 100, especially between 1 and 80, or even 2 to 20; and R2 to R6 being, independently of each other, carbon-based radicals, especially linear or branched hydrocarbon-based radicals (alkyl) containing 1 to 12 and especially 1 to 6 carbon atoms, and possibly comprising 1 to 4 heteroatoms, especially 0;

$R_b$ and $R_c$ are, independently of each other, chosen from:

a) carbon-based radicals, especially linear, branched and/or cyclic, saturated or unsaturated hydrocarbon-based radicals (alkyl), containing 1 to 18 carbon atoms, and possibly comprising 1 to 4 heteroatoms chosen from N, O, Si and S;

b) the radicals of formula:

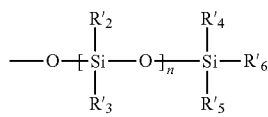

with n being between 0 and 100, especially between 1 and 80, or even 2 to 20; and $R'_2$ to $R'_6$ being, independently of each other, carbon-based radicals, especially linear or branched hydrocarbon-based radicals (alkyl), containing 1 to 12 and especially 1 to 6 carbon atoms, and possibly comprising 1 to 4 heteroatoms, especially 0; and ii) linear, branched and/or cyclic, saturated or unsaturated $C_1$-$C_{30}$ alkyl radicals, optionally comprising 1 to 3 heteroatoms chosen from O, S, F and N;

it being understood that at least one of the radicals R and/or R' is of formula (III).

The group A may especially be of formula:

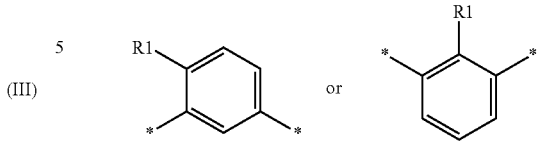

with R1 and the *s being as defined above.

In particular, R1 may be a methyl group, which leads to a group A of formula:

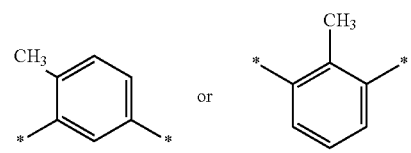

in which the *s are as defined above.

In particular, the compounds according to the invention may be in the form of a mixture linked to the fact that A may be a mixture of 2,4-tolylene and 2,6-tolylene, especially in (2,4 isomer)/(2,6 isomer) proportions ranging from 95/5 to 80/20.

According to the invention, at least one of the radicals R and/or R' should be of formula (III):

(III)

In this formula, L is preferably a divalent carbon-based radical, especially a linear, branched and/or cyclic, saturated or unsaturated hydrocarbon-based radical (alkylene), containing 1 to 18 carbon atoms, and possibly comprising 1 to 4 heteroatoms chosen from N, O and S. In the radical L, the carbon-based chain may be interrupted with the heteroatom(s) and/or may comprise a substituent comprising said heteroatom(s).

In particular, L may have the structure —$(CH_2)_n$- with n=1 to 18, especially 2 to 12 or even 3 to 8. Preferably, L is chosen from methylene, ethylene, propylene and butylene radicals and especially n-butylene or octylene.

The radical L may also be branched, for example of the type —$CH_2$—$CH(CH_3)$—, which leads to the radical of formula (III) below:

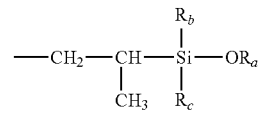

The radical $R_a$ may be a carbon-based radical, especially a linear, branched and/or cyclic, saturated or unsaturated hydrocarbon-based radical (alkyl), containing 1 to 18 carbon atoms, and possibly comprising 1 to 8 heteroatoms chosen from N, O, Si and S. The carbon-based chain may be interrupted with the heteroatom(s) and/or may comprise a substituent comprising said heteroatom(s); the heteroatoms may especially form one or more —SiO— (or —OSi—) groups.

Thus, the radical $R_a$ may have the structure —$(CH_2)n'$-$CH_3$ with $n'=0$ to 17, especially 1 to 12 or even from 1 to 6. In particular, $R_a$ may be methyl, ethyl, propyl or butyl.

It may also have the structure —$(CH_2)x$-O—$(CH_2)z$-$CH_3$ or —$(CH_2)x$-O—$(CH_2)y$-O—$(CH_2)z$-$CH_3$, with x=1 to 10, preferably 2; y=1 to 10, preferably 2, and z=0 to 10, preferably 0 or 1.

The radical $R_a$ may also have the structure —$SiR_4R_5R_6$ (in the case where n=0), in which $R_4$, $R_5$ and $R_6$ are, independently of each other, preferably alkyl radicals containing 1 to 12 carbon atoms and especially 1 to 6 carbon atoms; in particular, $R_4$, $R_5$ and/or $R_6$ may be chosen from methyl, ethyl, propyl and butyl.

The radical $R_a$ may also be a silicone radical of formula:

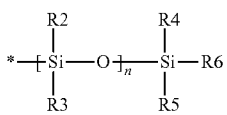

in which R2 to R6 are, independently of each other, preferably alkyl radicals containing 1 to 12 carbon atoms and especially 1 to 6 carbon atoms; in particular, R2 to R6 may be chosen from methyl, ethyl, propyl and butyl;

and in particular a radical:

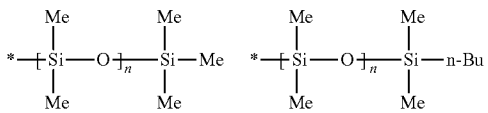

with n=1 to 100; and even more particularly a radical:

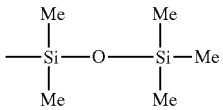

The radicals $R_b$ and $R_c$, which may be identical or different, may be carbon-based radicals, especially linear, branched and/or cyclic, saturated or unsaturated hydrocarbon-based radicals (alkyl), containing 1 to 18 carbon atoms, and possibly comprising 1 to 8 heteroatoms chosen from N, O, Si and S. In these radicals, the carbon-based chain may be interrupted with the heteroatom(s) and/or may comprise a substituent comprising said heteroatom(s); the heteroatoms may especially form one or more —SiO— (or —OSi—) groups.

Thus, they may have the structure —$(CH_2)m$-$CH_3$ with m=0 to 17, especially 1 to 12 or even 2 to 5; in particular, $R_b$ and/or $R_c$ may be methyl, ethyl, propyl or butyl.

They may also have the structure —O—$(CH_2)m'$-$CH_3$ with m'=0 to 5, especially 1 to 4 and in particular methoxy or ethoxy.

They may also have the structure —O—$(CH_2)x$-O—$(CH_2)z$-$CH_3$ or —O—$(CH_2)x$-O—$(CH_2)y$-O—$(CH_2)z$-$CH_3$, with x=1 to 10, preferably 2; y=1 to 10, preferably 2, and z=0 to 10, preferably 0 or 1.

They may also have the structure:

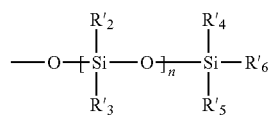

with n being between 0 and 100, especially between 1 and 80 or even 2 to 20;

and $R'_2$ to $R'_6$ being, independently of each other, preferably alkyl radicals containing 1 to 12 carbon atoms and especially 1 to 6 carbon atoms; in particular, $R'_2$ to $R'_6$ may be chosen from methyl, ethyl, propyl and butyl.

When they are of formula (III), the radicals R and/or R' are preferably chosen from the following radicals:

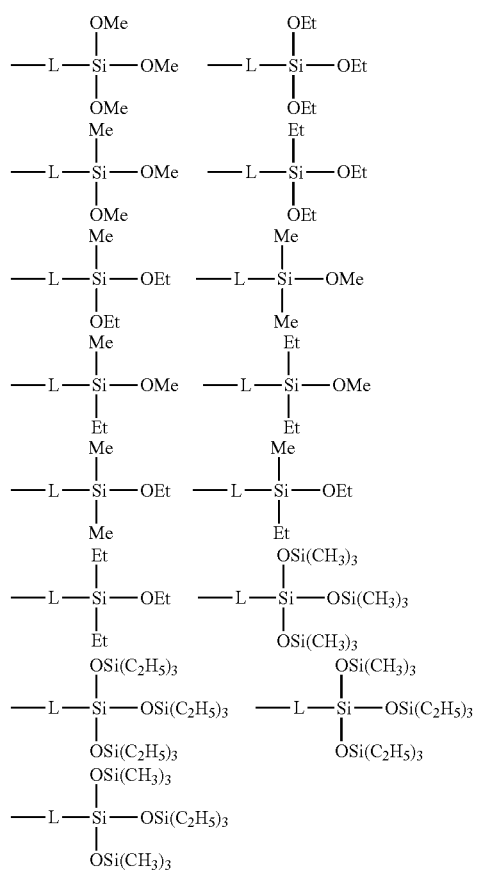

and also those of formula:

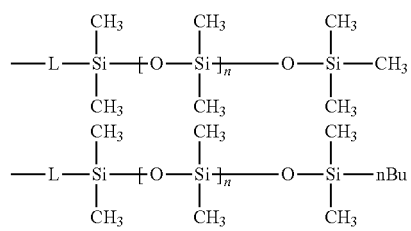

with n ranging from 0 to 100 and in particular

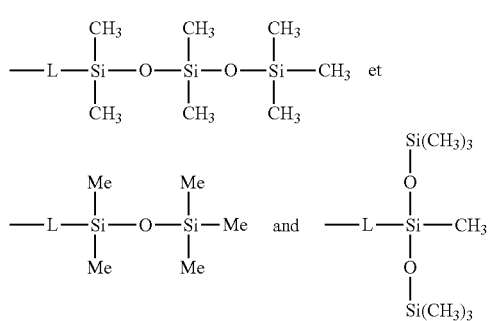

or alternatively

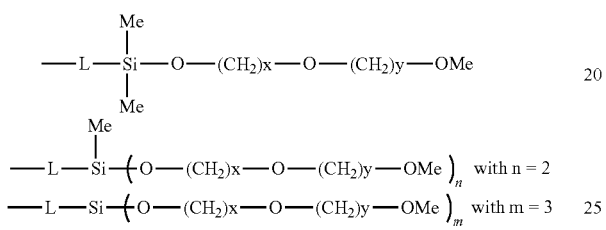

in which x=1 to 10, preferably 2; and y=1 to 10, preferably 2; and L being as defined above.

Preferably, in these formulae, L is a linear or branched $C_1$-$C_8$ alkylene radical, especially methylene, ethylene, propylene or butylene and especially n-butylene or octylene, or of formula —$CH_2$—$CH(CH_3)$—.

In one particular embodiment, R and R', which may be identical or different, are both of formula (III).

In another embodiment, one of the radicals R or R' represents a linear, branched and/or cyclic, saturated or unsaturated $C_1$-$C_{30}$ alkyl radical, optionally comprising 1 to 3 heteroatoms chosen from O, S, F and N.

This proves to be particularly advantageous for giving the compounds of formula (I) a universal nature, i.e. enabling them to texture, simultaneously, polar or apolar carbon-based media, linear or cyclic silicone media, and mixed oils, i.e. partially silicone-based carbon-based oils, and also mixtures thereof.

The carbon chain may be interrupted with the heteroatom(s) and/or may comprise a substituent comprising said heteroatom(s), especially in the form of a carbonyl group (—CO—), one or more hydroxyl radicals (—OH), and/or an ester radical —COOR" with R"=linear or branched alkyl radical containing 1 to 8 carbon atoms.

Thus, said radical R or R' may be a group chosen from:

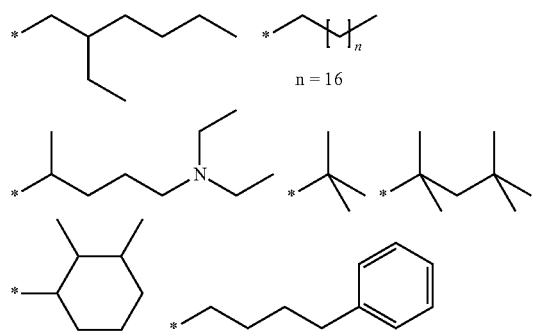

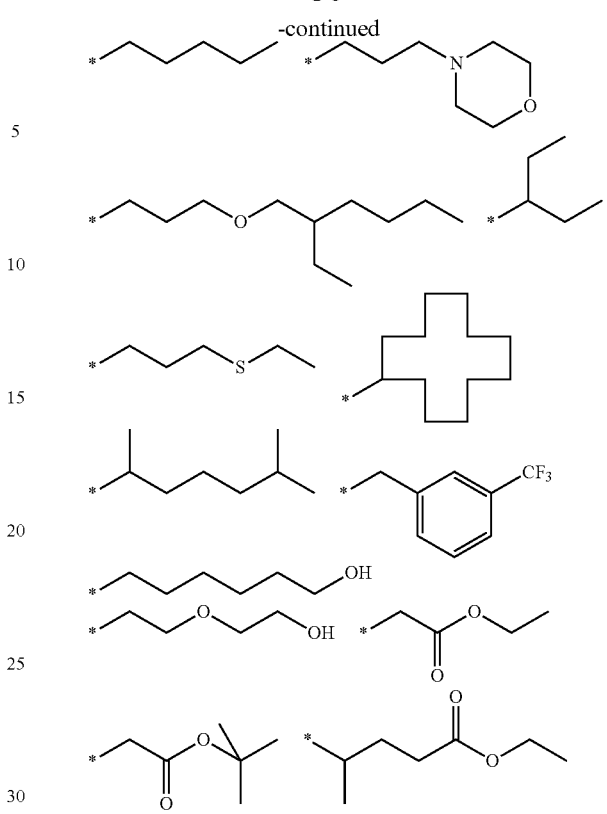

with * having the definition given above.

In one preferred embodiment, R or R' represents a branched, especially mono-branched, preferably acyclic, saturated or unsaturated alkyl radical containing 3 to 16 carbon atoms, especially 4 to 12 or even 4 to 8 carbon atoms, and optionally comprising 1 to 3 heteroatoms chosen from O, S, F and/or N, preferably O and/or N.

In particular, R or R' may be tert-butyl or 2-ethylhexyl radicals or of formula:

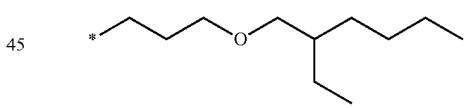

When the compound of formula (I) comprises a radical R that is an alkyl radical, and thus a radical R' that is of formula (III), the ratio between $n_R$ and $n_{R'}$ is preferably between 5/95 and 95/5, for example between 10/90 and 90/10, in particular between 40/60 and 85/15, especially between 50/50 and 80/20, or even between 60/40 and 75/25;

with $n_R$ being the number of moles of amine $NH_2$—R and $n_{R'}$ being the number of moles of amine $NH_2$—R' used to prepare the compound of formula (I).

The compounds according to the invention may be in the form of salts and/or of isomers of compounds of formula (I).

In general, the compounds of general formula (I) according to the invention may be prepared as described in patent application FR 2 910 809.

The compounds of silicone bis-urea type described above may be mixed with other non-silicone bis-urea compounds. According to a first aspect, the non-silicone bis-urea compounds may correspond to the general formula (II) below:

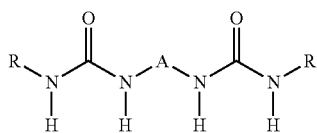

in which:

A is a group of formula:

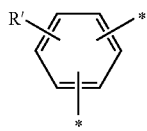

with R' being a linear or branched $C_1$ to $C_4$ alkyl radical and the *s symbolizing the points of attachment of the group A to each of the two nitrogen atoms of the residue of the compound of general formula (II), and R is a saturated or unsaturated, non-cyclic, mono-branched $C_6$ to $C_{15}$ alkyl radical whose hydrocarbon-based chain is optionally interrupted with 1 to 3 heteroatoms chosen from O, S and N, or a salt or isomer thereof.

According to one preferred embodiment of the invention, the group represented by A is a group of formula:

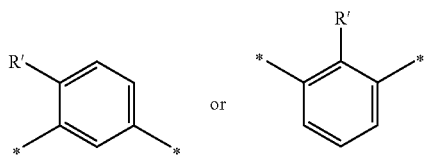

with R' and the *s being as defined above.

In particular, R' may be a methyl group, and the group A is then more particularly a group of formula:

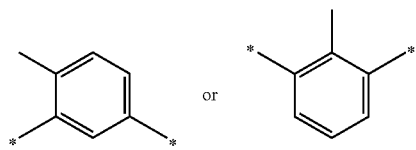

with the *s being as defined above.

According to a first embodiment of the invention, R may be chosen from the mono-branched radicals of general formula $C_nH_{2n+1}$, n being an integer ranging from 6 to 15, in particular from 7 to 9 or even equal to 8.

Thus, the two groups R of the compound of formula (II) may represent, respectively, a group:

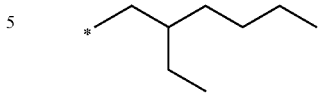

with * symbolizing the point of attachment of each of the groups R to each of the nitrogen atoms of the rest of the compound of general formula (II).

According to a second embodiment of the invention, R may be chosen from the mono-branched radicals of general formula $C_{m-p}H_{2m+1-2p}X_p$ being equal to 1, 2 or 3, preferably equal to 1, m being an integer ranging from 6 to 15, preferably from 10 to 14, in particular from 10 to 12, or even equal to 11, and X representing sulfur and/or oxygen atoms, in particular oxygen atoms.

More particularly, R may be a radical of formula $C_mH_{2m'}X-(C_{p'}H_{2p'}X')_r-C_xH_{2x+1}$, in which X and X' are, independently of each other, an oxygen or sulfur atom, preferably oxygen, r is 0 or 1, m', p' and x are integers such that their sum ranges from 6 to 15, in particular from 10 to 12, or even is equal to 11, and it being understood that at least one of the carbon-based chains $C_{m'}H_{2m'}$, $C_{p'}H_{2p'}$, or $C_xH_{2x+1}$ is branched.

Preferably, it is the chain $C_xH_{2x+1}$ that is branched, preferably r is equal to 0, preferably m' is an integer ranging from 1 to 10, especially from 2 to 6, in particular is equal to 3, and/or preferably x is an integer ranging from 4 to 16, especially from 6 to 12 and in particular is equal to 8.

Thus, the two groups R of the compound of formula (I) may represent, respectively, a group:

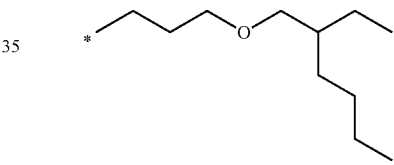

with * symbolizing the point of attachment of each of the groups R to each of the nitrogen atoms of the rest of the compound of general formula (I).

Such compounds may be present in the compositions according to the invention as mixtures with isomers, especially positional isomers on the group A, especially in 95/5 or 80/20 proportions.

As emerges from the examples below, the presence of one or the other of these radicals in the molecule of general formula (II) proves to be particularly advantageous for giving a universal nature, within the meaning of the invention, to the corresponding non-silicone bis-urea derivatives.

As non-limiting representations of the compounds that are most particularly suitable for the invention, mention may be made more particularly of the following compounds, used pure or as a mixture:

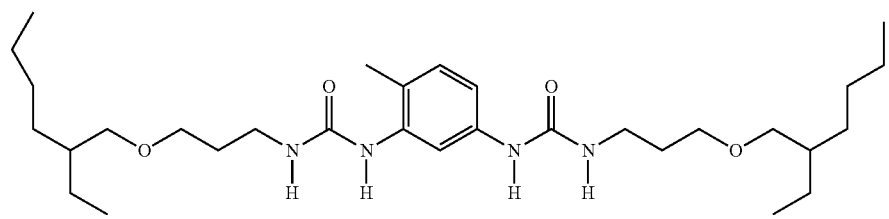

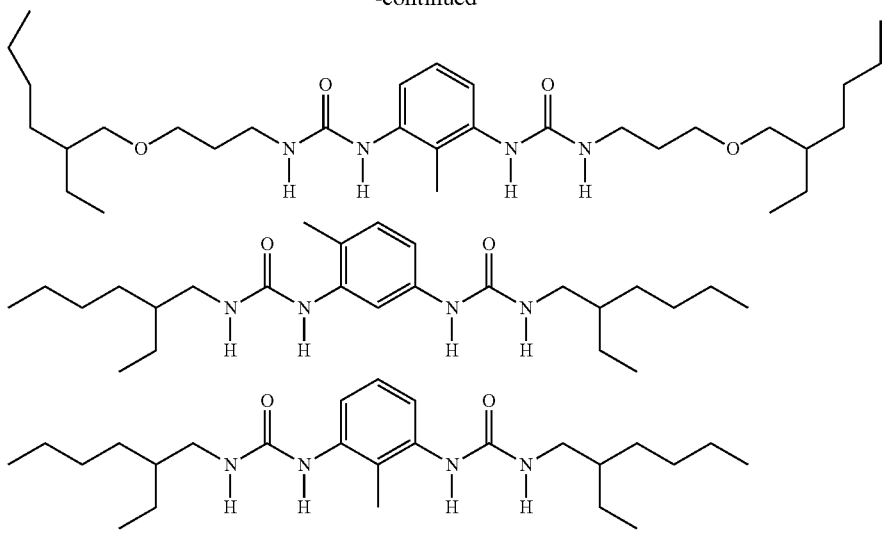

and the salts thereof.

According to another aspect of the invention, the non-silicone bis-urea derivatives of formula (III) below:

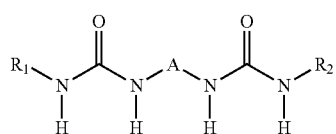

in which:
A is a group of formula:

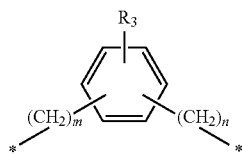

with
- $R_3$ being a hydrogen atom or a linear or branched $C_1$ to $C_4$ alkyl radical,
- n and m being, independently of each other, equal to 0 or 1, and
- * symbolizing the point of attachment of the group A to the two nitrogen atoms of the residue of the compound of general formula (III),
- $R_1$ is a saturated or unsaturated, non-cyclic branched $C_3$ to $C_{15}$ carbon-based radical optionally containing from 1 to 3 heteroatoms chosen from O, S, F and N and/or a carbonyl, and combinations thereof,
- $R_2$ is different from $R_1$ and is chosen from linear, branched or cyclic, saturated or unsaturated $C_1$-$C_{24}$ alkyl radicals optionally containing from 1 to 3 heteroatoms chosen from O, S, F and N, and optionally substituted with:
  1, 2 or 3 hydroxyl radicals,
  an ester radical (—COOR$_4$), with $R_4$ being a linear or branched alkyl radical containing from 1 to 8, especially 1 to 6 or even 2 to 4 carbon atoms;
  a saturated, unsaturated or aromatic cyclic radical containing from 5 to 12 carbon atoms, in particular a phenyl radical optionally substituted with one or more radicals, which may be identical or different, chosen from $C_1$-$C_4$ alkyl and trifluoromethyl radicals, or a morpholine derivative, and/or
  one or more linear or branched $C_1$-$C_4$ alkyl radicals, or a salt or isomer thereof.

In particular, n and m are equal, and more particularly equal to zero, and $R_3$ is a radical $R'_3$ as defined below. Thus, preferably, A represents a group

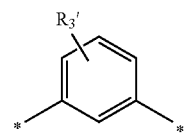

with $R_3'$ being a linear or branched $C_1$ to $C_4$ alkyl radical and * symbolizing the points of attachment of the group A to the two nitrogen atoms of the residue of the compound of general formula (III).

According to one variant of the invention, the compound of general formula (III) comprises, as A, at least one group chosen from:

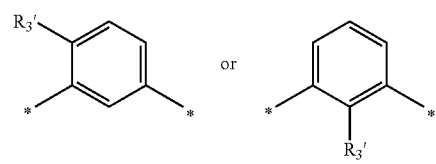

with $R_3'$ and * being as defined above.

In particular, $R_3'$ may be a methyl group, and in this case the group A represents a group

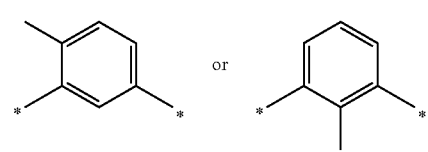

* being as defined above.

In particular, the compounds are such that A is a mixture of 2,4-tolylene and 2,6-tolylene, especially in (2,4 isomer)/(2,6 isomer) proportions ranging from 95/5 to 80/20.

According to one embodiment of the invention, the compound of general formula (III) comprises, as $R_1$, a branched $C_6$-$C_{15}$ radical.

According to one embodiment of the invention, the compound of general formula (III) comprises, as $R_1$, a group chosen from:

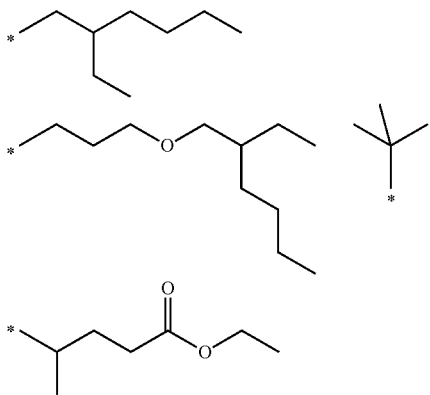

with * symbolizing the point of attachment of the group $R_1$ to the nitrogen of the residue of the compound of general formula (III).

As emerges from the examples below, the presence of one and/or the other of the two radicals in the molecule of general formula (III) proves to be particularly advantageous for giving a universal nature within the meaning of the invention to the corresponding asymmetric bis-urea derivatives.

As regards $R_2$, which is different from $R_1$, it may be advantageously chosen from the following groups:

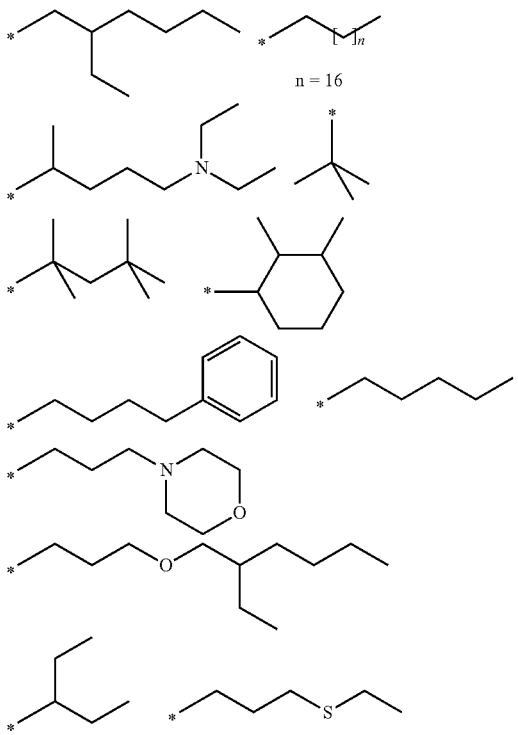

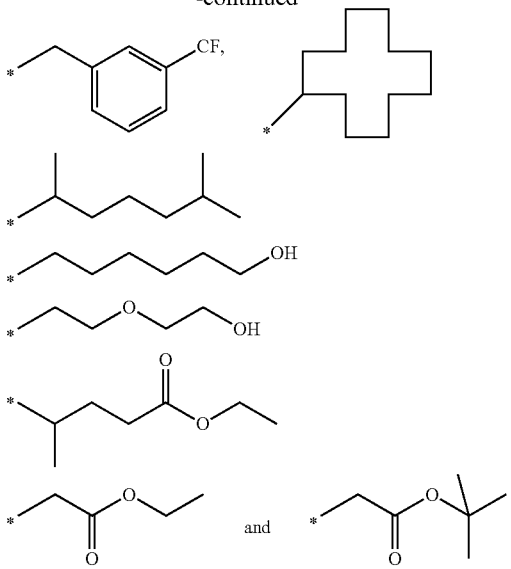

with * symbolizing the point of attachment of the group $R_2$ to the nitrogen of the residue of the compound of general formula (III).

In general, the compounds described may be prepared as described in patent application FR 2 910 809.

Block Polymers:

It is also possible to use, as fatty-phase rheological agent, grafted or sequenced block polymers.

It is especially possible to use grafted or sequenced block copolymers comprising at least one block of polyorganosiloxane type and at least one block of a free-radical polymer, for instance grafted copolymers of acrylic/silicone type, which may be used especially when the non-aqueous medium is a silicone phase.

It is also possible to use grafted or sequenced block copolymers comprising at least one block of polyorganosiloxane type and at least one block of a polyether. The polyorganopolysiloxane block may especially be a polydimethylsiloxane or a poly($C_2$-$C_{18}$)alkylmethylsiloxane; the polyether block may be a poly($C_2$-$C_{18}$)alkylene, in particular polyoxyethylene and/or polyoxypropylene. In particular, dimethicone copolyols or ($C_2$-$C_{18}$)alkyl dimethicone copolyols such as those sold under the name Dow Corning 3225C by the company Dow Corning, and lauryl methicones such as those sold under the name Dow Corning Q2-5200 by the company Dow Corning, may be used.

Grafted or sequenced block copolymers that may also be mentioned include those comprising at least one block resulting from the polymerization of at least one ethylenic monomer containing one or more optionally conjugated ethylenic bonds, for instance ethylene or dienes such as butadiene and isoprene, and of at least one block of a vinyl polymer and better still a styrene polymer. When the ethylenic monomer comprises several optionally conjugated ethylenic bonds, the residual ethylenic unsaturations after the polymerization are generally hydrogenated. Thus, in a known manner, the polymerization of isoprene leads, after hydrogenation, to the formation of an ethylene-propylene block, and the polymerization of butadiene leads, after hydrogenation, to the formation of an ethylene-butylene block. Among these polymers that may be mentioned are block copolymers, especially of "diblock" or "triblock" type such as polystyrene/polyisoprene (SI), polystyrene/polybutadiene (SB) such as those sold under the name Luvitol HSB by BASF, of the type such as polystyrene/copoly(ethylene-propylene) (SEP) such as those sold under the name Kraton by Shell Chemical Co or of the type such as polystyrene/copoly(ethylene-butylene) (SEB). Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS) and Kraton D-1107 (SIS) may be used in particular. The polymers are generally known as hydrogenated or non-hydrogenated diene copolymers.

Gelled Permethyl 99A-750, 99A-753-59 and 99A-753-58 (mixture of triblock and of star polymer), Versagel 5960 from Penreco (triblock+star polymer); OS129880, OS129881 and OS84383 from Lubrizol (styrene/methacrylate copolymer) may also be used.

As grafted or sequenced block copolymers comprising at least one block resulting from the polymerization of at least one ethylenic monomer containing one or more ethylenic bonds and of at least one block of an acrylic polymer, mention may be made of poly(methyl methacrylate)/polyisobutylene diblock or triblock copolymers or grafted copolymers containing a poly(methyl methacrylate) skeleton and polyisobutylene grafts.

As grafted or sequenced block copolymers comprising at least one block resulting from the polymerization of at least one ethylenic monomer containing one or more ethylenic bonds and of at least one block of a polyether such as a $C_2$-$C_{18}$ polyalkylene (especially polyethylene and/or polyoxypropylene), mention may be made of polyoxyethylene/polybutadiene or polyoxyethylene/polyisobutylene diblock or triblock copolymers.

Fatty Phase Gelling Silicone Elastomers

The term "elastomer" is intended to mean a deformable, flexible solid material having viscoelastic properties and in particular the consistency of a sponge. This elastomer is formed from high-molecular-weight polymeric chains, the mobility of which is limited by a uniform network of crosslinking points.

The elastomeric organopolysiloxanes used the composition according to the invention are preferably partially or totally crosslinked. They are in the form of particles. In particular, the particles of elastomeric organopolysiloxane have a size ranging from 0.1 to 500 µm, preferably from 3 to 200 µm and better still from 3 to 50 µm. These particles can have any shape and, for example, be spherical, flat or amorphous.

When they are included in an oily phase, these elastomeric organopolysiloxanes are converted, according to the amount of oily phase used, into a product which has a spongy appearance when they are used in the presence of low contents of oily phase, or into a homogeneous gel in the presence of higher amounts of oily phase. The gelling of the oily phase by these elastomers may be total or partial.

Thus, the elastomers of the invention can be conveyed in the form of an anhydrous gel consisting of an elastomeric organopolysiloxane and an oily phase. The oily phase used during the production of the anhydrous gel of elastomeric organopolysiloxane contains one or more oils that are liquid at ambient temperature (25° C.), chosen from hydrocarbon-based oils and/or silicone oils. Advantageously, the oily phase is a silicone liquid phase containing one or more oils chosen from polydimethylsiloxanes with a linear or cyclic chain, which are liquid at ambient temperature and which optionally comprise an alkyl or aryl chain that is pendant or at the end of a chain, the alkyl chain containing from 1 to 6 carbon atoms.

According to one embodiment, the elastomeric organopolysiloxanes used according to the invention can be obtained by addition and crosslinking reaction, in the presence of a catalyst, preferably a platinum catalyst, of at least:
(i) one organopolysiloxane having two vinyl groups in the α-ω position with respect to the silicone chain, per molecule; and
(ii) one organopolysiloxane having at least two hydrogen atoms bonded to a silicon atom, per molecule.

The first organopolysiloxane (i) is chosen from polydimethylsiloxanes; it is preferably an α-ω-dimethylvinylpolydimethylsiloxane.

The organopolysiloxane is preferably in a gel obtained according to the following steps:
(a) mixing of the first and second organopolysiloxanes (i) and (ii);
(b) addition of an oily phase to the mixture of step (a);
(c) polymerization of the first and second organopolysiloxanes (i) and (ii) in the oily phase in the presence of a catalyst, preferably a platinum catalyst.

According to one embodiment, the crosslinked organopolysiloxane can be obtained by polymeric addition reaction of an organohydrogenopolysiloxane of formula (I) with an organopolysiloxane of formula (II) and/or an unsaturated hydrocarbon-based chain of formula (III).

According to one variant, the crosslinked organopolysiloxane is obtained by polymeric reaction of an organohydrogenopolysiloxane of formula (I) with an organopolysiloxane of formula (II).

Organohydrogenopolysiloxane of Formula (I)

The organohydrogenopolysiloxane of formula (I) comprises at least one structural unit chosen from the group composed of an $SiO_2$ unit, an $HSiO_{1.5}$ unit, an $RSiO_{1.5}$ unit, an RHSiO unit, an $R_2SiO$ unit, an $R_3SiO_{0.5}$ unit and an $R_2HSiO_{0.5}$ unit, the R group being, in these units, a monovalent hydrocarbon-based chain containing from 1 to 16 carbon atoms that may be substituted or unsubstituted, but which is distinct from an unsaturated aliphatic group, and which has on average at least 1.5 hydrogen atoms bonded to a silicon atom.

The R group in the organohydrogenopolysiloxane of formula (I) may be an alkyl group containing from 1 to 16, preferably from 10 to 16 carbon atoms. This R group may, for example, be a methyl group, an ethyl group, a propyl group, a lauryl group, a myristyl group or a palmityl group.

The R group in the organohydrogenopolysiloxane of formula (I) may also be an aryl group, such as a phenyl or tolyl group.

The R group still in the organohydrogenopolysiloxane of formula (I) may also be a monovalent hydrocarbon-based chain comprising a cycloalkyl group, such as cyclohexyl, or else a hydrocarbon-based chain substituted with one, two or more groups chosen from a halogen atom, such as chlorine, bromine or fluorine, and a cyano group, for example an α-trifluoropropyl or chloromethyl group.

In particular, at least 30 mol % of the R groups are preferably methyl groups, and from 5 to 50 mol %, preferably from 10 to 40 mol %, of the R groups are a hydrocarbon-based chain containing from 10 to 16 carbon atoms.

The hydrocarbon-based chain may then advantageously comprise at least one lauryl group, or even the majority of the R groups may be lauryl groups.

The organohydrogenopolysiloxane of formula (I) may be linear, branched or cyclic.

The organohydrogenopolysiloxane of formula (I) preferably contains from 2 to 50 and even more preferably from 2 to 10 hydrogen atoms bonded to a silicon atom (Si—H). The content of hydrogen atoms bonded to a silicon atom in this compound of formula (I) conventionally varies from 0.5 to 50 mol %, and even more preferably from 1 to 20 mol %, relative to the total sum of the hydrogen atoms and of all the organic groups bonded to a silicon atom.

Organopolysiloxane of Formula (II)

The organopolysiloxane of formula (II) comprises at least one structural unit chosen from the group composed of an $SiO_2$ unit, a $(CH_2\!=\!CH)SiO_{1.5}$ unit, an $RSiO_{1.5}$ unit, an $R(CH_2\!=\!CH)SiO$ unit, an $R_2SiO$ unit, an $R_3SiO_{0.5}$ unit and an $R_2(CH_2\!=\!CH)SiO_{0.5}$ unit, the R group being as defined in formula (I) and having, on average, at least 1.5 vinyl groups bonded to a silicon atom.

This compound preferably contains from 2 to 50 vinyl groups bonded to a silicon atom. The average number of vinyl groups bonded to a silicon atom preferably varies from 2 to 10, and even more preferably from 2 to 5.

Preferably, at least 30 mol % of the R groups are methyl groups and 5 to 50 mol %, preferably 10 to 40 mol %, of the R groups are a hydrocarbon-based chain containing from 10 to 16 carbon atoms.

The organopolysiloxane of formula (II) may be linear, branched or cyclic.

The content of vinyl group in the compound of formula (II) preferably ranges between 0.5 and 50 mol %, even more preferably from 1 to 20 mol %, relative to all the organic groups bonded to a silicon atom.

Optionally unsaturated hydrocarbon-based chain of formula (III)

The unsaturated hydrocarbon-based chain of formula (III) corresponds to the following formula:

$$C_mH_{2m-1}(CH_2)_xC_mH_{2m-1}$$

in which:
m is an integer ranging from 2 to 6, and
x is an integer at least equal to 1.
x is preferably an integer ranging from 1 to 20.

By way of example of this compound of formula (III), mention may be made of pentadiene, hexadiene, heptadiene, octadiene, pentadecadiene, heptadecadiene and pentatriacontadiene.

The polymeric addition reactions are described in detail in document US 2004/0234477.

Among the crosslinked organopolysiloxanes, crosslinked polyalkyldimethylsiloxanes are preferred. The term "polyalkyldimethylsiloxane" is intended to mean a linear organopolysiloxane of formula (IV)

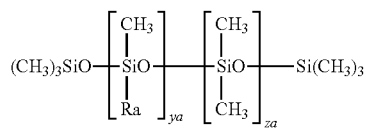

comprising monovalently or divalently bonded grafts of formula (V)

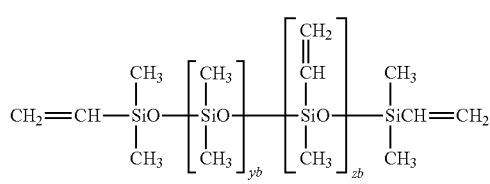

in which:
Ra is an alkyl group containing from 10 to 16 carbon atoms, and can preferably be a lauryl group,
ya is an integer ranging from 1 to 100,
za is an integer ranging from 1 to 100,
yb is an integer ranging from 1 to 100,
zb is an integer ranging from 1 to 100.

The term "divalently bonded" is intended to mean bonded to two distinct organopolysiloxanes of formula (IV). In other words, it involves a bridge between two linear chains as defined by formula (IV).

As nonemulsifiable elastomers that can be used according to the invention, use is preferably made of dimethicone/vinyl dimethicone copolymers (INCI name: Dimethicone/Vinyl Dimethicone Crosspolymer), and vinyl dimethicone/alkyl dimethicone copolymers, for instance vinyl dimethicone/lauryl dimethicone copolymers (INCI name: Vinyl Dimethicone/Lauryl Dimethicone Crosspolymer).

As nonemulsifying elastomers that can be used according to the invention, mention may be made of:
  those having the INCI name Dimethicone/Vinyl Dimethicone Crosspolymer (and) C12-14 Pareth-12: for instance those sold under the name DC 9509 by the company Dow Corning,
  those having the INCI name Dimethicone/Vinyldimethicone Crosspolymer: for instance those sold under the name DC9505 or DC 9506 by the company Dow Corning, those having the INCI name Cyclomethicone (and) Dimethicone/Vinyldimethicone Crosspolymer: for instance those sold under the name KSG-15® by Shin-Etsu, methyl trimethicone (and) dimethicone/vinyl dimethicone crosspolymer: those sold by Shin-Etsu under the name KSG-1610®,
  those having the INCI name Dimethicone (and) Dimethicone/Vinyl Dimethicone Crosspolymer: for instance those sold under the name KSG-16® by Shin-Etsu, Isododecane (and) Dimethicone/Vinyldimethicone Crosspolymer: those sold under the name USG-106® by Shin-Etsu,
  those having the INCI name Vinyl Dimethicone/Lauryl Dimethicone Crosspolymer: KSG-41® (in a mineral oil), KSG-42® (in isododecane), KSG-43® (in triethylhexanoin) and KSG-44® (in squalane), sold by Shin-Etsu.

As nonemulsifying elastomer, mention may also be made of spherical nonemulsifying silicone elastomers in the form of an elastomeric crosslinked organopolysiloxane powder coated with silicone resin, in particular with silsesquioxane resin, as described, for example, in U.S. Pat. No. 5,538,793. Such elastomers are sold under the names KSP-100, KSP-101, KSP-102, KSP-103, KSP-104 and KSP-105 by the company Shin Etsu.

Other elastomeric crosslinked organopolysiloxanes in the form of spherical powders may be powders of hybrid silicone functionalized with fluoroalkyl groups, in particular sold under the name KSP-200 by the company Shin Etsu; powders of hybrid silicones functionalized with phenyl groups, in particular sold under the name KSP-300 by the company Shin Etsu.

In the compositions according to the invention, use may also be made of elastomers of silicones with an MQ group, such as those sold by the company Wacker under the names Belsil RG100, Belsil RPG33 and preferentially RG80. These particular elastomers, where they are in combination with the resins according to the invention, can make it possible to improve the transfer resistance properties of the compositions containing them.

It is also possible to mention, as lipophilic thickeners, also called gelling agents, that can be used in a composition of the invention, ethylcellulose, for instance the product sold under the name Ethocel® by the company Dow Chemical; polycondensates of polyamide type resulting from condensation between a dicarboxylic acid containing at least 32 carbon atoms and an alkylene diamine, and in particular ethylenediamine, in which the polymer comprises at least one terminal carboxylic acid group esterified or amidated with at least one monoalcohol or one monoamine containing from 12 to 30 carbon atoms, which are linear and saturated, and in particular ethylenediamine/stearyl dilinoleate copolymers, such as the product sold under the name Uniclear 100 VG® by the company Arizona Chemical; crosslinked acrylamide polymers and copolymers; galactomannans comprising from one to six, and in particular from two to four, hydroxyl groups per monosaccharide, which are substituted with a saturated or unsaturated alkyl chain, for instance guar gum alkylated with $C_1$ to $C_6$, and in particular $C_1$ to $C_3$, alkyl chains, and mixtures thereof.

As lipophilic thickeners suitable for the invention, mention may also be made of copolymers of the polystyrene/polyalkylene type, and more particularly "diblock", "triblock" or "radial" block copolymers of the polystyrene/polyisoprene or polystyrene/polybutadiene type, such as those sold under the name Luvitol HSB® by the company BASF, of the polystyrene/copoly(ethylene-propylene) type, such as those sold under the name Kraton® by the company Kraton Polymers, or else of the polystyrene/copoly(ethylene-butylene) type, blends of triblock and radial (star) copolymers in isododecane, such as those sold by the company Penreco under the name Versagel®, for instance the blend of butylene/ethylene/styrene triblock copolymer and of ethylene/propylene/styrene star copolymer in isododecane (Versagel M 5960).

Among the lipophilic thickeners that can be used in a cosmetic composition of the invention, mention may also be made of fatty acid esters of dextrin, such as dextrin palmitates, in particular those sold under the names Rheopearl TL® or Rheopearl KL® by the company Chiba Flour, hydrogenated plant oils, such as hydrogenated castor oil, fatty alcohols, in particular $C_8$ to $C_{26}$, and more particularly $C_{12}$ to $C_{22}$, fatty alcohols, for instance myristyl alcohol, cetyl alcohol, stearyl alcohol, behenyl alcohol, or else polyvinyl alcohol.

Thickeners that may also be mentioned include glyceryl poly(meth)acrylate polymers; polyvinylpyrrolidone; associative polymers, and in particular associative polyurethanes; polysaccharide alkyl ethers (in particular in which the alkyl group contains from 1 to 24 carbon atoms, preferably from 1 to 10, better still from 1 to 6, and more especially from 1 to 3), such as those described in document EP-A-898958.

Waxes

The composition according to the invention may also comprise at least one wax.

For the purpose of the present invention, the term "wax" is intended to mean a lipophilic compound which is solid at ambient temperature (25° C.), with a reversible solid/liquid change of state, which has a melting point of greater than or equal to 30° C., which may be up to 120° C.

The melting point of the wax can be measured using a differential scanning calorimeter (D.S.C.), for example the calorimeter sold under the name DSC 30 by the company Mettler.

The waxes may be hydrocarbon-based waxes, fluoro waxes and/or silicon waxes and may be of plant, mineral, animal and/or synthetic origin. In particular, the waxes have a melting point of greater than 25° C. and better still greater than 45° C.

The wax or the mixture of waxes is present in a content at least equal to 7% by weight. Preferably, it is present in a content ranging from 10% to 40% by weight, relative to the total weight of the composition, better still from 15% to 35% and even better still from 16% to 30% by weight.

Preferably, the waxes are chosen from beeswax, lanolin wax and Chinese insect waxes; rice wax, carnauba wax, ouricury wax, esparto grass wax, cork fiber wax, sugarcane wax, Japan wax and sumach wax; montan wax, microcrystalline waxes, paraffins; polyethylene waxes, waxes obtained by Fischer-Tropsch synthesis, waxes obtained by catalytic hydrogenation of animal or plant oils having linear or branched, C8-C32 fatty chains, fluoro waxes, wax obtained by hydrogenation of olive oil esterified with stearyl alcohol, waxes obtained by hydrogenation of castor oil esterified with cetyl alcohol, and tacky waxes.

Hydrocarbon-based waxes, for instance beeswax, lanolin wax and Chinese insect waxes; rice wax, carnauba wax, ouricury wax, esparto grass wax, cork fiber wax, sugarcane wax, Japan wax and sumach wax; montan wax, microcrystalline waxes, paraffins; polyethylene waxes, waxes obtained by Fischer-Tropsch synthesis and waxy copolymers, and also esters thereof, may in particular be used.

Mention may also be made of waxes obtained by catalytic hydrogenation of animal or plant oils having linear or branched, C8-C32 fatty chains.

Among these waxes, mention may in particular be made of hydrogenated jojoba oil, hydrogenated sunflower oil, hydrogenated castor oil, hydrogenated copra oil and hydrogenated lanolin oil, bis(1,1,1-trimethylolpropane) tetrastearate sold under the name Hest 2T-4S by the company Heterene, and bis(1,1,1-trimethylolpropane)tetrabehenate sold under the name Hest 2T-4B by the company Heterene.

Mention may also be made of fluoro waxes.

The wax obtained by hydrogenation of olive oil esterified with stearyl alcohol, sold under the name Phytowax Olive 18 L 57, or alternatively waxes obtained by hydrogenation of castor oil esterified with cetyl alcohol, sold under the name Phytowax ricin 16L64 and 22L73, by the company Sophim, may also be used. Such waxes are described in application FR-A-2792190.

Mention may also be made of:
silicone waxes, in particular substituted linear polysiloxanes; mention may be made, for example, of silicone polyether waxes, alkyl dimethicones or alkoxy dimethicones containing from 16 to 45 carbon atoms, and alkyl methicones, for instance the $C_{30}$-$C_{45}$ alkyl methicone sold under the trade name AMS C 30 by Dow Corning,
hydrogenated oils that are solid at 25° C., such as hydrogenated castor oil, hydrogenated jojoba oil, hydrogenated palm olive, hydrogenated tallow, hydrogenated coconut oil and fatty esters that are solid at 25° C., for instance the $C_{20}$-$C_{40}$ alkyl stearate sold under the trade name Kester Wax K82H by the company Koster Keunen,
and/or mixtures thereof.

According to one embodiment, the wax present in the composition according to the invention may be totally or partially in powder form, in particular micronized powder form, so as to facilitate its use in the preparation of the cosmetic composition.

Among the waxes that can be used in powder form, mention may in particular be made of the carnauba wax microbeads sold under the name Microcare 350® by the company Micro Powders and the paraffin wax microbeads sold under the name Microease 114S® sold by the company Micro Powders. Such additional micronized waxes make it possible in particular to improve the properties during application of the composition to the skin.

Hydrophilic Gelling Agents:

The composition according to the invention may also comprise at least one hydrophilic gelling agent, also subsequently referred to as hydrophilic thickener.

These thickeners may be used alone or in combination. These thickeners may in particular be chosen from cellulosic polymers and gums.

The term "hydrophilic thickener" is intended to mean a thickening agent that is water-soluble or water-dispersible.

As hydrophilic thickeners, mention may in particular be made of water-soluble or water-dispersible thickening polymers. They may in particular be chosen from:
polyvinylpyrrolidone,
polyvinyl alcohol,
modified or unmodified carboxyvinyl polymers, such as the products sold under the name Carbopol (CTFA name: carbomer) by the company Goodrich;
homopolymers or copolymers of acrylic acid or methacrylic acid or salts thereof and esters thereof, and in particular the products sold under the names Versicol F® or Versicol K® or Salcare SC95 by the company Allied Colloid, Ultrahold 8® by the company Ciba-Geigy, polyacrylates and polymethacrylates, such as the products sold under the names Lubrajel and Norgel by the company Guardian or under the name Hispagel by the company Hispano Chimica, polyacrylic acids of Synthalen K type;

polyacrylamides;

copolymers of acrylic acid and of acrylamide sold in the form of their sodium salt under the names Reten® by the company Hercules, poly(sodium methacrylate) sold under the name Darvan No 7® by the company Vanderbilt, the sodium salts of polyhydroxycarboxylic acids sold under the name Hydagen F® by the company Henkel;

2-acrylamido-2-methylpropanesulfonic acid polymers and copolymers, which are optionally crosslinked and/or neutralized, for instance the poly(2-acrylamido-2-methylpropanesulfonic acid) sold by the company Clariant under the name Hostacerin AMPS (CTFA name: ammonium polyacryldimethyltauramide);

crosslinked anionic acrylamide/AMPS copolymers, in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC;

polyacrylic acid/alkyl acrylate copolymers of Pemulen type;

polysaccharide biopolymers, for instance xanthan gum, guar gum, gum Arabic, locus bean gum, acacia gum, scleroglucans, chitin derivatives and chitosan derivatives, carrageenans, gellans, alginates, or celluloses such as microcrystalline cellulose, carboxymethylcellulose, hydroxymethylcellulose, hydroxyethylcellulose and hydroxypropylcellulose;

hydrophilic fumed silicas obtained by high-temperature hydrolysis of a volatile silicon compound in an oxyhydrogen flame, producing a finely divided silica. The hydrophilic silicas have a large number of silanol groups at their surface. Such hydrophilic silicas are, for example, sold under the names Aerosil 130®, Aerosil 200®, Aerosil 255®, Aerosil 300® and Aerosil 380® by the company Degussa, or Cab-O-Sil HS-5®, Cab-O-Sil EH-5®, Cab-O-Sil LM-130®, Cab-O-Sil MS-55® and Cab-O-Sil M-5® by the company Cabot. They preferably have a particle size that can be nanometric to micrometric, for example ranging from about 5 to 200 nm;

hydrophilic clays;

associative polymers, for instance the PEG-150/stearyl alcohol/SMDI copolymer sold under the name Aculyn 46 by Rohm & Haas, or the steareth-100/PEG-136/HDI copolymer sold under the name Rheolate FX 1100 by Elementis;

and mixtures thereof.

The hydrophilic thickener may be chosen from associative polymers. For the purpose of the present invention, the term "associative polymer" is intended to mean any amphiphilic polymer comprising, in its structure, at least one fatty chain and at least one hydrophilic portion. The associative polymers in accordance with the present invention may be anionic, cationic, nonionic or amphoteric.

Among the associative anionic polymers, mention may be made of those comprising at least one hydrophilic unit, and at least one fatty-chain allyl ether unit, more particularly from those in which the hydrophilic unit is made up of an unsaturated ethylenic anionic monomer, more particularly of a vinylcarboxylic acid and most particularly of an acrylic acid, a methacrylic acid or mixtures thereof, and in which the fatty-chain allyl ether unit corresponds to the monomer of formula (I) below:

$$CH_2=C(R')CH_2OB_nR \quad (I)$$

in which R' denotes H or $CH_3$, B denotes the ethyleneoxy radical, n is zero or denotes an integer ranging from 1 to 100, and R denotes a hydrocarbon-based radical chosen from alkyl, arylalkyl, aryl, alkylaryl and cycloalkyl radicals containing 8 to 30 carbon atoms, preferably 10 to 24, and even more particularly from 12 to 18 carbon atoms.

Anionic amphiphilic polymers of this type are described and prepared, according to an emulsion polymerization process, in patent EP-0 216 479.

As associative anionic polymers, mention may also be made of anionic polymers comprising at least one hydrophilic unit of olefinic unsaturated carboxylic acid type, and at least one hydrophobic unit exclusively of unsaturated carboxylic acid ($C_{10}$-$C_{30}$) alkyl ester type. By way of example, mention may be made of the anionic polymers described and prepared according to U.S. Pat. Nos. 3,915,921 and 4,509,949.

As cationic associative polymers, mention may be made of quaternized cellulose derivatives and polyacrylates containing amine side groups.

The nonionic associative polymers may be chosen from:

celluloses modified with groups comprising at least one fatty chain, for instance hydroxyethylcelluloses modified with groups comprising at least one fatty chain, such as alkyl groups, in particular $C_8$-$C_{22}$ alkyl groups, arylalkyl groups and alkylaryl groups, such as Natrosol Plus Grade 330 CS($C_{16}$ alkyls) sold by the company Aqualon, celluloses modified with polyalkylene glycol alkylphenyl ether groups, guars such as hydroxypropyl guar, modified with groups comprising at least one fatty chain such as an alkyl chain, copolymers of vinylpyrrolidone and of fatty-chain hydrophobic monomers, copolymers of $C_1$-$C_6$ alkyl methacrylates or acrylates and of amphiphilic monomers comprising at least one fatty chain, copolymers of hydrophilic methacrylates or acrylates and of hydrophobic monomers comprising at least one fatty chain, for instance the polyethylene glycol methacrylate/lauryl methacrylate copolymer, associative polyurethanes, mixtures thereof.

Preferably, the associative polymer is chosen from associative polyurethanes. Associative polyurethanes are nonionic block copolymers comprising, in the chain, both hydrophilic blocks usually of polyoxyethylene nature and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendant chains or chains at the end of a hydrophilic block. In particular, it is possible for one or more pendant chains to be provided. In addition, the polymer may comprise a hydrocarbon-based chain at one or both ends of a hydrophilic block. The associative polyurethanes may be blocked in triblock or multiblock form. The hydrophobic blocks may thus be at each end of the chain (for example: triblock copolymer with a hydrophilic central block) or distributed both at the ends and within the chain (multiblock copolymer for example). These polymers may also be graft polymers or star polymers. Preferably, the associative polyurethanes are triblock copolymers in which the hydrophilic block is a polyoxyethylene chain comprising from 50 to 1000 oxyethylene groups. In general, the associative polyurethanes comprise a urethane bond between the hydrophilic blocks, whence the name.

By way of example of the associative polymers that can be used in the invention, mention may be made of the polymer $C_{16}$-$OE_{120}$-$C_{16}$ from the company Servo Delden (under the name SER AD FX1100, which is a molecule containing a urethane function and having a weight-average molecular weight of 1300), OE being an oxyethylene unit. An associative polymer that may also be used is Rheolate 205 containing a urea function, sold by the company Rheox, or else Rheolate 208 or 204 or else Rheolate FX 1100 by Elementis. These associative polyurethanes are sold in pure form. The product DW 1206B from Rohm & Haas containing a $C_{20}$ alkyl chain and with a urethane bond, sold at a solids content of 20% in water, may also be used.

It is also possible to use solutions or dispersions of these polymers, in particular in water or in an aqueous-alcoholic medium. By way of example of such polymers, mention may be made of SER AD FX1010, SER AD FX1035 and SER AD 1070 from the company Servo Delden, Rheolate 255, Rheolate 278 and Rheolate 244 sold by the company RHEOX. It is also possible to use the products Aculyn 46, DW 1206F and DW 1206J, and also Acrysol RM 184 or Acrysol 44 from the company Rohm & Haas, or alternatively Borchigel LW 44 from the company Borchers.

Dyestuffs

The composition according to the invention may also comprise at least one dyestuff.

The dyestuff may be chosen from pulverulent dyestuffs (in particular pigments and pearlescent agents), water-soluble dyestuffs or liposoluble dyestuffs.

The term "pigments" should be understood to mean white or colored, mineral or organic particles of any shape, which are insoluble in the physiological medium and are intended to color the composition.

The term "pearlescent agents" should be understood to mean iridescent particles of any shape, in particular produced by certain mollusks in their shell, or else synthesized.

The pigments may be white or colored, and mineral and/or organic. Among mineral pigments, mention may be made of optionally surface-treated titanium dioxide, zirconium oxide or cerium oxide, and also zinc oxide, iron oxide (black, yellow or red) or chromium oxide, manganese violet, ultramarine blue, chromium hydrate and Prussian blue, metal powders such as aluminum powder or copper powder.

Among organic pigments, mention may be made of carbon black, D & C type pigments, and lakes based on cochineal carmine, barium, strontium, calcium or aluminum.

Mention may also be made of pigments with an effect, such as particles comprising an organic or mineral, natural or synthetic substrate, for example glass, acrylic resins, polyester, polyurethane, polyethylene terephthalate, ceramics or aluminas, said substrate being optionally coated with metal substances such as aluminum, gold, silver, platinum, copper or bronze, or with metal oxides, for instance titanium dioxide, iron oxide, chromium oxide and mixtures thereof.

The pearlescent pigments can be chosen from white pearlescent pigments, such as mica coated with titanium or with bismuth oxychloride, colored pearlescent pigments, such as titanium mica coated with iron oxides, titanium mica coated with in particular Prussian blue or with chromium oxide, titanium mica coated with an organic pigment of the above-mentioned type, and also pearlescent pigments based on bismuth oxychloride. Interference pigments, in particular liquid-crystal or multilayer interference pigments, may also be used.

The term "alkyl" mentioned in the compounds mentioned above denotes in particular an alkyl group containing from 1 to 30 carbon atoms, preferably containing from 5 to 16 carbons atoms. Hydrophobically-treated pigments are in particular described in application EP-A-1086683.

The pulverulent dyestuffs as described above can be totally or partially surface-treated with a hydrophobic agent, in particular a compound of silicone nature, a compound of fluorinated nature, a compound of fluoro-silicone nature, a fatty acid, or an amino acid, or a mixture thereof.

The term "silicone compound" is intended to mean a compound comprising at least one silicon atom. The term "fluorinated compound" is intended to mean a compound comprising at least one fluorine atom.

The term "fluoro-silicone compound" is intended to mean a compound comprising at least one fluorine atom and at least one silicon atom.

By way of example, the hydrophobic treatment agent may be chosen from silicones such as methicones, dimethicones, perfluoroalkylsilanes, perfluoroalkylsilazanes, triethoxycaprylylsilane, triethoxysilylethylpolydimethylsiloxyethylhexyl dimethicone; fatty acids, such as stearic acid; metal soaps, such as aluminum dimyristate, the aluminum salt of hydrogenated tallow glutamate; perfluoroalkyl phosphates, polyhexafluoropropylene oxides, polyorganosiloxanes comprising perfluoroalkyl groups, perfluoropolyethers, silicone-grafted acrylic polymers (in particular described in application JP-A-05-339125, the content of which is incorporated by way of reference); amino acids; N-acylated amino acids or salts thereof; lecithin, isopropyl titanium triisostearate, isostearyl sebacate, and mixtures thereof.

The surface-treated pulverulent dyestuffs can be prepared according to surface treatment techniques of chemical, electronic, mechanochemical or mechanical nature which are well known to those skilled in the art. Commercial products may also be used.

The surface agent may be absorbed or adsorbed onto the pulverulent dyestuffs by solvent evaporation, chemical reaction or creation of a covalent bond.

According to one variant, the surface treatment consists of a coating of the pulverulent dyestuffs.

The coating may represent from 1% to 300% by weight of the weight of the untreated pulverulent dyestuffs, for example from 5% to 200%, in particular from 10% to 100% by weight of the weight of untreated pulverulent dyestuffs.

The coating may represent from 0.1% to 10% by weight, and in particular from 1% to 5% by weight of the total weight of the coated pulverulent dyestuff.

The coating can be carried out, for example, by adsorption of a liquid surface agent at the surface of the pulverulent dyestuffs by simple mixing, with stirring, of said pulverulent dyestuffs and of said surface agent, optionally hot mixing, prior to the incorporation of the particles into the other ingredients of the makeup or care composition.

The coating can be carried out, for example, by chemical reaction of a surface agent with the surface of the pulverulent dyestuffs and creation of a covalent bond between the surface agent and the pulverulent dyestuffs. This method is in particular described in U.S. Pat. No. 4,578,266.

The chemical surface treatment may consist in diluting the surface agent in a volatile solvent, in dispersing the pulverulent dyestuffs in this mixture, and then in slowly evaporating off the volatile solvent, in such a way that the surface agent is deposited at the surface of the pulverulent dyestuffs.

Fluorinated Surface Agent

The solid particles can be totally or partially surface-treated with a compound of fluorinated nature.

The fluorinated surface agents may be chosen from perfluoroalkyl phosphates, perfluoropolyethers, polytetrafluoropolyethylene (PTFE) and perfluoroalkanes.

The perfluoropolyethers are in particular described in patent application EP-A-486135, and sold under the trade names Fomblin by the company Montefluos.

Some perfluoroalkyl phosphates are in particular described in application JP H05-86984. The perfluoroalkyl phosphate-diethanolamines sold by Asahi Glass under the reference AsahiGuard AG530 may be used.

The perfluoroalkanes may be linear or cyclic perfluoroalkanes. Among the linear perfluoroalkanes, mention may be made of the linear alkane series, such as perfluorooctane, perfluorononane or perfluorodecane. Among the cyclic perfluoroalkanes, mention may be made of perfluorocycloalkanes, perfluoro(alkylcycloalkanes), perfluoropolycycloalkanes, and aromatic perfluorinated hydrocarbons (perfluoroarenes). Among the perfluoroalkanes, mention may also be made of perfluorinated hydrocarbon-based organo compounds comprising at least one heteroatom.

Among the perfluorocycloalkanes and perfluoro(alkylcycloalkanes), mention may be made of perfluorodecalin sold under the name Flutec PP5 GMP by the company Rhodia, perfluoro(methyldecalin), and perfluoro(C3-C5 alkyl cyclohexanes) such as perfluoro(butylcyclohexane).

Among the perfluoropolycycloalkanes, mention may be made of bicyclo[3.3.1]nonane derivatives, such as perfluorotrimethylbicyclo[3.3.1]nonane, adamantane derivatives, such as perfluorodimethyladamantane, and perfluoro derivatives of hydrogenated phenanthrene, such as tetracosafluorotetradecahydrophenanthrene.

Among the perfluoroarenes, mention may be made of perfluoro derivatives of naphthalene, for instance perfluoronaphthalene and perfluoromethyl-1-naphthalene.

By way of example of commercial references of pigments and of fillers treated with a fluorinated compound, mention may be made of:
- the yellow iron oxide/perfluoroalkyl phosphate sold in particular under the reference PF 5 Yellow 601 by the company Daito Kasei,
- the red iron oxide/perfluoroalkyl phosphate sold in particular under the reference PF 5 Red R 516L by the company Daito Kasei,
- the black iron oxide/perfluoroalkyl phosphate sold in particular under the reference PF 5 Black BL 100 by the company Daito Kasei,
- the titanium dioxide/perfluoroalkyl phosphate sold in particular under the reference PF 5 TiO2 CR 50 by the company Daito Kasei,
- the yellow iron oxide/perfluoropolymethyl isopropyl ether sold in particular under the reference iron oxide yellow BF-25-3 by the company Toshiki,
- the DC Red 7/perfluoropolymethyl isopropyl ether sold in particular under the reference D&C Red 7 FHC by the company Cardre Inc.,
- the DC Red 6/PTFE sold in particular under the reference T 9506 by the company Warner-Jenkinson.

Fatty Acid or Amino Acid Treatment Agent

The hydrophobic treatment agent can be chosen from fatty acids, such as stearic acid; metal soaps, such as aluminum dimyristate, the aluminum salt of hydrogenated tallow glutamate; amino acids; N-acylated amino acids or salts thereof; lecithin, isopropyl titanium triisostearate (also known as ITT), and mixtures thereof.

The N-acylated amino acids can comprise an acyl group containing from 8 to 22 carbon atoms, such as, for example, a 2-ethylhexanoyl, caproyl, lauroyl, myristoyl, palmitoyl, stearoyl or cocoyl group. The salts of these compounds may be the aluminum, magnesium, calcium, zirconium, zinc, sodium or potassium salts. The amino acid may, for example, be lysine, glutamic acid or alanine.

The fatty acids are, in the present invention, in particular acids having hydrocarbon-based chains containing from 1 to 30 carbon atoms, preferably containing from 5 to 18 carbon atoms. The hydrocarbon-based chain may be saturated, monounsaturated or polyunsaturated.

By way of example of fatty acid-coated pigments, mention may be made of those sold under the trade reference NAI-TAO-77891, NAI-C33-8073-10, NAI-C33-8075, NAI-C47-051-10, NAI-C33-115, NAI-C33-134, NAI-C33-8001-10, NAI-C33-7001-10, NAI-C33-9001-10 from the company Miyoshi Kasei.

The water-soluble dyes are, for example, beetroot juice and methylene blue.

The synthetic or natural liposoluble dyes are, for example, DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

The dyestuffs, in particular the pigments that have been treated with a hydrophobic agent, may be present in the composition in a content ranging from 0.1% to 50% by weight, relative to the total weight of the composition, preferably ranging from 0.5% to 30% by weight, and preferentially ranging from 1% to 20% by weight.

Film-Forming Polymers

The composition according to the invention may also comprise at least one film-forming polymer.

In the present invention, the term "film-forming polymer" is intended to mean a polymer that is capable of forming, by itself or in the presence of an auxiliary film-forming agent, a macroscopically continuous film that adheres to keratin materials, and preferably a cohesive film, and even better still a film of which the cohesion and the mechanical properties are such that said film can be isolated and handled in isolation, for example when said film is produced by pouring onto a non-stick surface, for instance a Teflon-coated or silicone-coated surface.

In combination with the mixtures of MQ and propyl T resins, the film-forming polymer(s) used can be conveyed in the oily phase (liposoluble or lipodispersible polymers) or conveyed in an aqueous phase (water-soluble polymers or latex).

The composition may comprise an aqueous phase and the film-forming polymer may be present in this aqueous phase. In this case, said polymer will preferably be a polymer in an aqueous dispersion (latex) or a water-soluble polymer.

Among the film-forming polymers that may be used in the composition of the present invention, mention may be made of synthetic polymers, of free-radical type or of polycondensate type, and polymers of natural origin, and blends thereof.

As examples of water-soluble film-forming polymers, mention may be made of:
- proteins, for instance proteins of plant origin, such as wheat or soybean proteins; proteins of animal origin, such as keratins, for example keratin hydrolyzates and sulfonic keratins;
- cellulose polymers, such as hydroxyethylcellulose, hydroxypropylcellulose, methylcellulose, ethylhydroxyethylcellulose, carboxymethylcellulose, and also quaternized cellulose derivatives;
- acrylic polymers or copolymers, such as polyacrylates or polymethacrylates;
- vinyl polymers, for instance polyvinylpyrrolidones, copolymers of methyl vinyl ether and of maleic anhydride, the copolymer of vinyl acetate and of crotonic acid, copolymers of vinylpyrrolidone and of vinyl acetate; copolymers of vinylpyrrolidone and of caprolactam; polyvinyl alcohol;
- anionic, cationic, amphoteric or nonionic chitin or chitosan polymers;
- gum arabics, guar gum, xanthan derivatives and karaya gum;
- alginates and carrageenans;
- glycosaminoglycans, hyaluronic acid and its derivatives;
- shellac resin, sandarac gum, dammar resins, elemi gums and copal resins;
- deoxyribonucleic acid;
- mucopolysaccharides such as chondroitin sulfates;
- and mixtures thereof.

The film-forming polymer may also be present in the composition in the form of particles in dispersion in an aqueous phase, generally known as latex or pseudolatex. The techniques for preparing these dispersions are well known to those skilled in the art.

Aqueous dispersions of film-forming polymer that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Allianz Opt® by the company Rohm and Haas, the aqueous dispersions of acrylic or styrene/acrylic polymers sold under the name Joncryl® by the company Johnson Polymer or else the aqueous polyurethane dispersions sold under the names Neorez R-981® and Neorez R-974® by the company Avecia-Neoresins, Avalure UR-405®, Avalure UR-410®, Avalure UR-425®, Avalure UR-450®, Sancure 875®, Avalure UR-445® and Sancure 2060® by the company Noveon, Impranil 85® by the company Bayer, Aquamere H-1511® by the company Hydromer; the sulfopolyesters sold under the trade mark Eastman AQ® by the company Eastman Chemical Products, vinyl dispersions, for instance Mexomer PAM® from the company Chimex, aqueous dispersions of polyvinyl acetate, for instance Vinybran® from the company Nisshin Chemical or those sold by the company Union Carbide, aqueous dispersions of vinylpyrrolidone, dimethylaminopropylmethacrylamide and lauryldimethylpropylmethacrylamidoammonium chloride terpolymer, such as Styleze W from ISP, aqueous dispersions of polyurethane/polyacrylic hybrid polymers such as those sold under the references Hybridur® by the company Air Products or Duromer® from National Starch, and dispersions of core/shell type; for example, those sold by the company Atofina under the reference Kynar (core: fluoro; shell: acrylic) or alternatively those described in document U.S. Pat. No. 5,188,899 (core: silica; shell: silicone), and mixtures thereof.

The composition may comprise an oily phase, and the film-forming polymer may be present in this oily phase. The polymer may then be in a dispersion or in solution.

As examples of nonaqueous dispersions of lipodispersible film-forming polymers in the form of nonaqueous dispersions of polymer particles in one or more silicone and/or hydrocarbon-based oils and which can be surface-stabilized with at least one stabilizer, in particular a block, grafted or random polymer, mention may be made of acrylic dispersions in isododecane, for instance Mexomer PAP® from the company Chimex, and dispersions of particles of a grafted ethylenic, preferably acrylic, polymer in a liquid fatty phase, the ethylenic polymer being advantageously dispersed in the absence of additional stabilizer at the surface of the particles, as described in particular in document WO 04/055081.

Among the film-forming polymers that can be used in the composition of the present invention, mention may be made of synthetic polymers, of free-radical type or of polycondensate type, polymers of natural origin, and blends thereof.

The term "free-radical film-forming polymer" is intended to mean a polymer obtained by polymerization of unsaturated, in particular ethylenically unsaturated, monomers, each monomer being capable of homopolymerizing (unlike polycondensates).

The film-forming polymers of free-radical type may in particular be vinyl polymers or copolymers, in particular acrylic polymers.

The vinyl film-forming polymers can result from the polymerization of ethylenically unsaturated monomers having at least one acid group and/or esters of these acid monomers and/or amides of these acid monomers.

Monomers bearing an acid group that can be used include α,β-ethylenically unsaturated carboxylic acids, such as acrylic acid, methacrylic acid, crotonic acid, maleic acid or itaconic acid. (Meth)acrylic acid and crotonic acid are preferably used, and more preferentially (meth)acrylic acid.

The esters of acid monomers are advantageously chosen from the esters of (meth)acrylic acid (also known as (meth) acrylates), in particular alkyl(meth)acrylates, in particular C1-C30, preferably C1-C20, alkyl(meth)acrylates, aryl (meth)acrylates, in particular C6-C10 aryl(meth)acrylates, and hydroxyalkyl(meth)acrylates, in particular C2-C6 hydroxyalkyl(meth)acrylates.

Among the alkyl(meth)acrylates, mention may be made of methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl(meth)acrylates, mention may be made of hydroxyethyl acrylate, 2-hydroxypropyl acrylate, hydroxyethyl methacrylate and 2-hydroxypropyl methacrylate.

Among the aryl(meth)acrylates, mention may be made of benzyl acrylate and phenyl acrylate.

The esters of (meth)acrylic acid that are particularly preferred are alkyl(meth)acrylates.

According to the present invention, the alkyl group of the esters may be either fluorinated or perfluorinated, i.e. a part or all of the hydrogen atoms of the alkyl group are substituted with fluorine atoms.

As amides of the acid monomers, mention may, for example, be made of (meth)acrylamides, and in particular N-alkyl(meth)acrylamides, in particular C2-C12 alkyl(meth) acrylamides. Among the N-alkyl(meth)acrylamides, mention may be made of N-ethylacrylamide, N-t-butylacrylamide, N-t-octylacrylamide and N-undecylacrylamide.

The vinyl film-forming polymers may also result from the homopolymerization or the copolymerization of monomers chosen from vinyl esters and styrene monomers. In particular, these monomers may be polymerized with acid monomers and/or esters thereof and/or amides thereof, such as those mentioned above.

As an example of vinyl esters, mention may be made of vinyl acetate, vinyl neodecanoate, vinyl pivalate, vinyl benzoate and vinyl t-butyl benzoate.

As styrene monomers, mention may be made of styrene and alpha-methylstyrene.

Among the film-forming polycondensates, mention may be made of polyurethanes, polyesters, polyester amides, polyamides, epoxy ester resins, and polyureas.

The polyurethanes may be chosen from anionic, cationic, nonionic or amphoteric polyurethanes, polyurethane-acrylics, polyurethane-polyvinylpyrrolidones, polyester-polyurethanes, polyether-polyurethanes, polyureas, polyurea-polyurethanes, and mixtures thereof.

The polyesters may be obtained, in a known manner, by condensation of dicarboxylic acids with polyols, in particular diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers can be used alone or as a combination of at least two dicarboxylic acid monomers. Among these monomers, phthalic acid, isophthalic acid and terephthalic acid are preferentially chosen.

The diol may be chosen from aliphatic, alicyclic and aromatic diols. Use is preferably made of a diol chosen from: ethylene glycol, diethylene glycol, triethylene glycol, 1,3-propanediol, cyclohexane dimethanol and 4-butanediol. Other polyols that may be used include glycerol, pentaerythritol, sorbitol and trimethylolpropane.

The polyesteramides can be obtained in a manner analogous to the polyesters, by a polycondensation of diacids with diamines or aminoalcohols. Diamines that may be used include ethylenediamine, hexamethylenediamine, meta- or para-phenylenediamine. Monoethanolamine may be used as amino alcohol.

According to one example of a composition according to the invention, the film-forming polymer may be a polymer solubilized in a liquid fatty phase comprising organic oils or solvents (the film-forming polymer is then said to be a liposoluble polymer). Preferably, the liquid fatty phase comprises a volatile oil, optionally as a mixture with a non-volatile oil.

By way of example of liposoluble polymers, mention may be made of copolymers of a vinyl ester (the vinyl group being directly connected to the oxygen atom of the ester group and the vinyl ester having a linear or branched, saturated hydrocarbon-based radical, containing from 1 to 19 carbon atoms, bonded to the carbonyl of the ester group) and of at least one other monomer which may be a vinyl ester (other than the vinyl ester already present), an α-olefin (containing from 8 to 28 carbon atoms), an alkyl vinyl ether (of which the alkyl group contains from 2 to 18 carbon atoms), or an allyl or methallyl ester (having a linear or branched, saturated hydrocarbon-based radical, containing from 1 to 19 carbon atoms, bonded to the carbonyl of the ester group).

These polymers may be crosslinked by means of crosslinking agents which can either be of the vinyl type, or of the allyl or methallyl type, such as tetraallyloxyethane, divinylbenzene, divinyl octanedioate, divinyl dodecanedioate and divinyl octadecanedioate.

As examples of these polymers, mention may be made of the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% of divinylbenzene, vinyl dimethylpropionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene crosslinked with 0.2% of divinylbenzene, and allyl propionate/allyl stearate crosslinked with 0.2% of divinylbenzene.

As additional examples of liposoluble film-forming polymers, mention may be made of copolymers of a vinyl ester and at least one other monomer, which may be a vinyl ester, in particular vinyl neodecanoate, vinyl benzoate and vinyl t-butylbenzoate, an α-olefin, an alkyl vinyl ether, or an allyl or methallyl ester.

As liposoluble film-forming polymers, mention may also be made of liposoluble copolymers, and in particular those resulting from the copolymerization of vinyl esters containing from 9 to 22 carbon atoms or of alkyl acrylates or methacrylates, the alkyl radicals containing from 10 to 20 carbon atoms.

Such liposoluble copolymers may be chosen from copolymers of polyvinyl stearate, of polyvinyl stearate crosslinked with the aid of divinylbenzene, of diallyl ether or of diallyl phthalate, and copolymers of polystearyl(meth)acrylate, of polyvinyl laurate, of polylauryl(meth)acrylate, it being possible for these poly(meth)acrylates to be crosslinked with the aid of ethylene glycol dimethacrylate or tetraethylene glycol dimethacrylate.

The liposoluble copolymers defined above are known and are described in particular in application FR-A-2232303; they may have a weight-average molecular weight ranging from 2000 to 500 000 and preferably from 4000 to 200 000.

As liposoluble film-forming polymers that can be used in the invention, mention may also be made of polyalkylenes and in particular copolymers of C2-C20 alkenes, such as polybutene, alkylcelluloses with a linear or branched, saturated or unsaturated C1 to C8 alkyl radical, for instance ethylcellulose and propylcelullose, copolymers of vinylpyrrolidone (VP) and in particular copolymers of vinylpyrrolidone and of C2 to C40 and better still C3 to C20 alkene. By way of example of VP copolymers that can be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecane, VP/triacontene, VP/styrene or VP/acrylic acid/lauryl methacrylate.

Mention may also be made of silicone resins, which are generally soluble or swellable in silicone oils, which are crosslinked polyorganosiloxane polymers.

By way of examples of polymethylsilsesquioxane resins that are commercially available, mention may be made of those which are sold by the company Wacker under the reference Resin MK, such as Belsil PMS MK, or by the company Shin-Etsu under the references KR-220L.

By way of examples of polypropylsilsesquioxane resins that are commercially available, mention may be made of those which are sold under the reference DC670 by the company Dow Corning.

Siloxysilicate resins that may be mentioned include trimethyl siloxysilicate (TMS) resins such as those sold under the reference SR1000 by the company General Electric or under the reference TMS 803 by the company Wacker. Mention may also be made of the timethyl siloxysilicate resins sold in a solvent such as cyclomethicone, sold under the name KF-7312J by the company Shin-Etsu, and DC 749 and DC 593 by the company Dow Corning.

Mention may also be made of copolymers of silicone resins such as those mentioned above with polydimethylsiloxanes, for instance the pressure-sensitive adhesive copolymers sold by the company Dow Corning under the reference Bio-PSA and described in document U.S. Pat. No. 5,162,410, or else the silicone copolymers which result from the reaction of a silicone resin, such as those described above, and of a diorganosiloxane as described in document WO 2004/073626.

Mention may also be made of acrylic/silicone grafted copolymers having a vinyl, methacrylic or acrylic polymeric backbone, and organosiloxane or polyorganosiloxane pendant grafts. Such polymers are in particular described in U.S. Pat. No. 4,693,935, U.S. Pat. No. 4,981,903 and U.S. Pat. No. 4,981,902.

Preferably, these polymers comprise monomers A, C and, optionally, B, for which:

A is at least one vinyl, methacrylate or acrylate monomer which can polymerize under free radical conditions;

B, when it is present, is at least one stiffening monomer which can copolymerize with A;

C is a monomer of the following formula:

$$X(Y)_n Si(R)_{3-m} Z_m$$

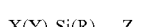

where X is a vinyl group which can copolymerize with the monomers A and B;

Y is a divalent linker;

n is 0 or 1;

m is an integer between 1 and 3;

R is a hydrogen atom, an alkyl radical containing from 1 to 10 carbon atoms, a substituted or unsubstituted phenyl radical, or an alkoxy radical containing from 1 to 10 carbon atoms;

Z is a monovalent siloxane polymeric group.

Examples of monomers A are lower to intermediate esters of methacrylic acid and of linear- or branched-chain C1-C12 alcohols, styrene, vinyl esters, vinyl chloride, vinylidene chloride, or acryloyl monomers.

Examples of monomers B are polar acrylic or methacrylic monomers having at least one hydroxyl, amino, ester or ionic group (for instance quaternary ammoniums, the carboxylate salt or acids such as carboxylic acids, acrylic acids, or sulfonic acid or its salts).

The monomer C is defined above.

As examples of acrylic/silicone grafted copolymers, mention may be made of those sold by 3M under the reference 3M Silicones Plus VS70 Dry Polymer®, having the INCI name: Polysilicone-6, or else KP-561® sold by Shin-Etsu and having the INCI name: Acrylates/Stearyl Acrylate/Dimethicone Methacrylate Copolymer, or KP-562® sold by Shin-Etsu and having the INCI name: Acrylates/Behenyl Acrylate/Dimethicone Acrylate Copolymer.

According to one exemplary embodiment of the invention, the film-forming polymer is a film-forming linear block ethylenic polymer which preferably comprises at least a first block and at least a second block having different glass transition temperatures (Tg), said first and second blocks being connected to one another via an intermediate block comprising at least one constituent monomer of the first block and at least one constituent monomer of the second block.

Advantageously, the first and second blocks of the block polymer are not compatible with one another.

Such polymers are described, for example, in documents EP 1411069 or WO 04/028488.

The film-forming polymer may be chosen from block or random polymers and/or copolymers comprising in particular polyurethanes, polyacrylics, silicones, fluoro polymers, butyl gums, ethylene copolymers, natural gums and polyvinyl alcohols, and mixtures thereof. The monomers of the block or random copolymers comprising at least one combination of monomers of which the polymer results in a glass transition temperature of less than ambient temperature (25° C.) can be chosen in particular from butadiene, ethylene, propylene, acrylic, methacrylic, isoprene, isobutene, a silicone, and mixtures thereof.

The composition according to the invention may also comprise at least one film-forming polymer chosen from vinyl polymers comprising at least one unit derived from a carbosiloxane dendrimer.

The vinyl polymer may in particular have a backbone and at least one side chain, which comprises a carbosiloxane dendrimer structure. The term "carbosiloxane dendrimer structure", in the context of the present invention, represents a molecular structure having branched groups with high molecular weights, said structure having high regularity in the radial direction starting from the backbone bond. Such carbosiloxane dendrimer structures are described in the form of a highly branched siloxane-silylalkylene copolymer in the laid-open Japanese patent application Kokai 9-171 154.

The vinyl polymer may be one of the polymers described in the examples of application EP0963751 or, for example, the product TIB-4-200 sold by Dow Corning.

Mention may also be made, as film-forming polymers, of systems with two components, such as compounds X and Y, defined hereinafter, capable of polymerizing in situ, at atmospheric pressure and ambient temperature, and of forming films which are advantageously biocompatible, non-tacky, slightly opalescent or even peelable. Such systems are in particular partly described in documents WO 01/96 450 and GB 2 407 496 from Dow Corning.

According to one particular embodiment, the compounds X and the compounds Y are silicone compounds. The compounds X and Y may be aminated or nonaminated.

According to another embodiment, at least one of the compounds X and Y is a polymer of which the main chain is formed predominantly from organosiloxane units.

Among the silicone compounds mentioned hereinafter, some may exhibit both film-forming and adhesive properties, according, for example, to their proportion of silicone or according to whether they are used as a mixture with a particular additive. It is consequently possible to modulate the film-forming properties or the adhesive properties of such compounds according to the use envisioned; this is in particular the case for "room temperature vulcanization" reactive elastomeric silicones.

The compounds X and Y can react together at a temperature ranging between ambient temperature and 180° C. Advantageously, the compounds X and Y are capable of reacting together at ambient temperature (20±5° C.) and atmospheric pressure, or advantageously in the presence of a catalyst, via a hydrosilylation reaction or a condensation reaction, or a crosslinking reaction in the presence of a peroxide.

According to one particular embodiment, the compounds X and Y react by hydrosilylation in the presence of a catalyst.

Advantageously, the compounds X and Y are chosen from silicone compounds capable of reacting by hydrosilylation in the presence of a catalyst; in particular, the compound X is chosen from polyorganosiloxanes comprising units of formula (I) described below, and the compound Y is chosen from organosiloxanes comprising alkylhydrogenosiloxane units of formula (III) described below.

According to one particular embodiment, the compound X is a polydimethylsiloxane comprising vinyl end groups, and the compound Y is a polymethylhydrogenosiloxane.

The compound X is therefore advantageously chosen from polyorganosiloxanes comprising siloxane units of formula:

in which:
R represents a linear or cyclic, monovalent hydrocarbon-based group containing from 1 to 30 carbon atoms, preferably from 1 to 20, and better still from 1 to 10 carbon atoms, for instance a short-chain alkyl radical containing, for example, from 1 to 10 carbon atoms, in particular a methyl radical or else a phenyl group, preferably a methyl radical,
m is equal to 1 or 2, and
R' represents:
an unsaturated aliphatic hydrocarbon-based group containing from 2 to 10, preferably from 3 to 5 carbon atoms, for instance a vinyl group or a group —R"—CH=CHR'" in which R" is a divalent aliphatic hydrocarbon-based chain containing from 1 to 8 carbon atoms, which is bonded to the silicon atom, and R'" is a hydrogen atom or an alkyl radical containing from 1 to 4 carbon atoms, preferably a hydrogen atom; as R' group, mention may be made of vinyl and allyl groups and mixtures thereof; or
an unsaturated cyclic hydrocarbon-based group containing from 5 to 8 carbon atoms, for instance a cyclohexenyl group.

Preferably, R' is an unsaturated aliphatic hydrocarbon-based group, preferably a vinyl group.

According to one embodiment, R represents an alkyl radical containing from 1 to 10 carbon atoms or else a phenyl group, and preferably a methyl radical, and R' is a vinyl group.

The compound Y may be advantageously chosen from polyorganosiloxanes comprising at least one alkylhydrogenosiloxane unit of the formula below:

in which:
R represents a linear or cyclic, monovalent hydrocarbon-based group containing from 1 to 30 carbon atoms, for instance an alkyl radical containing from 1 to 30 carbon atoms, preferably from 1 to 20 and better still from 1 to 10 carbon atoms, in particular a methyl radical, or else a phenyl group, and p is equal to 1 or 2. Preferably, R is a hydrocarbon-based group, preferably methyl.

According to one embodiment, the compositions comprising the compound X and/or Y may also comprise an additional reactive compound such as:
organic or mineral particles comprising at their surface at least 2 unsaturated aliphatic groups; mention may, for example, be made of silicas surface-treated, for example, with silicone compounds comprising vinyl groups, for instance cyclotetramethyltetravinylsiloxane-treated silica, silazane compounds, such as hexamethyldisilazane.

The hydrosilylation reaction is carried out in the presence of a catalyst which may be present with one or other of the compounds X or Y or be present in isolation. For example, this catalyst may be present in the composition in an encapsulated form if the two compounds X and Y, of which it must bring about the interaction, are present in this same composition, in a nonencapsulated form, or, conversely, it may be present therein in a nonencapsulated form if at least one of the compounds X and Y is present in the composition in an encapsulated form. The catalyst is preferably platinum-based or tin-based.

The catalyst may be present in a content ranging from 0.0001% to 20% by weight, relative to the total weight of the composition comprising it.

The compounds X and/or Y may be combined with polymerization inhibitors or retarders, and more particularly catalyst inhibitors. In a nonlimiting manner, mention may be made of cyclic polymethylvinylsiloxanes, and in particular tetravinyltetramethylcyclotetrasiloxane, acetylenic, preferably volatile, alcohols, such as methylisobutanol.

The presence of ionic salts, such as sodium acetate, may have an influence on the rate of polymerization of the compounds.

By way of example of a combination of compounds X and Y reacting by hydrosilylation in the presence of a catalyst, mention may be made of the following references proposed by the company Dow Corning: DC7-9800 Soft Skin Adhesive Parts A & B, and also the combination of the following mixtures A and B prepared by Dow Corning:

| Mixture A: | | | |
|---|---|---|---|
| Ingredient (INCI name) | CAS No. | Contents (%) | Function |
| Dimethyl siloxane, dimethylvinylsiloxy-terminated | 68083-19-2 | 55-95 | Polymer |
| Silica silylate | 68909-20-6 | 10-40 | Filler |
| 1,3-Diethenyl-1,1,3,3-tetramethyldisiloxane complexes | 68478-92-2 | Trace | Catalyst |
| Tetramethyldivinyldisiloxane | 2627-95-4 | 0.1-1 | Polymer |

| Mixture B: | | | |
|---|---|---|---|
| Ingredient (INCI name) | CAS No. | Contents (%) | Function |
| Dimethyl siloxane, dimethylvinylsiloxy-terminated | 68083-19-2 | 55-95 | Polymer |
| Silica silylate | 68909-20-6 | 10-40 | Filler |
| Dimethyl, methylhydrogen siloxane, trimethylsiloxy-terminated | 68037-59-2 | 1-10 | Polymer |

The compound X may represent from 0.1% to 95% by weight, relative to the total weight of the composition containing it, preferably from 1% to 90%, and better still from 5% to 80%.

The compound Y may represent from 0.1% to 95% by weight, relative to the total weight of the composition containing it, preferably from 1% to 90% and better still from 5% to 80%.

The composition according to the invention may comprise a plasticizer which promotes the formation of a film with the film-forming polymer. Such a plasticizer may be chosen from all the compounds known to those skilled in the art as being capable of performing the desired function.

Ionic Surfactants

The composition according to the invention may also comprise at least one ionic surfactant.

The surfactant may be lipophilic and/or hydrophilic, used alone or in combination. The surfactant may be chosen from anionic, cationic and amphoteric surfactants.

The surfactant may be present in the composition according to the invention in a content ranging from 0.1% to 10% by weight, relative to the total weight of the composition, and preferably ranging from 0.5% to 8% by weight, and preferentially ranging from 0.5% to 7% by weight.

Preferably, the ionic surfactants are chosen from cationic surfactants, amphoteric surfactants, carboxylates, taurates and N-acyl N-methyltaurates, alkyl sulfoacetates, polypeptides, anionic derivatives of alkyl polyglycoside, salts of C16-C30 fatty acids deriving from amines, polyoxyethylenated fatty acid salts, phosphoric esters and their salts, sulfosuccinates, alkyl sulfates, isethionates and N-acylisethionates, acylglutamates, soybean derivatives, citrates, proline derivatives, lactylates, sarcosinates, sulfonates and glycinates.

When the ionic surfactant is an anionic surfactant, it is chosen from:
 carboxylates, such as sodium 2-(2-hydroxyalkyloxy)acetate;
 taurates and N-acyl N-methyltaurates;
 alkyl sulfoacetates;
 polypeptides;
 anionic derivatives of alkyl polyglycoside (acyl-D-galactoside uronate);
 salts of C16-C30 fatty acids, in particular those deriving from amines, for instance triethanolamine stearate and/or 2-amino-2-methyl-1,3-propanediol stearate;
 salts of polyoxyethylenated fatty acids, in particular those deriving from amines or the alkali metal salts, and mixtures thereof;
 phosphoric esters and salts thereof, such as DEA oleth-10 phosphate (Crodafos N 10N from the company Croda) or monocetyl monopotassium phosphate (Amphisol K from Givaudan);
 sulfosuccinates, such as Disodium PEG-5 citrate lauryl sulfosuccinate and disodium ricinoleamido MEA sulfosuccinate;
 alkyl sulfates;
 isethionates and N-acylisethionates;
 acylglutamates, such as disodium hydrogenated tallow glutamate (Amisoft HS-21 R® sold by the company Ajinomoto) and sodium stearoyl glutamate (Amisoft HS-11 PF® sold by the company Ajinomoto) and mixtures thereof;
 soybean derivatives, such as potassium soyate;
 citrates, such as glyceryl stearate citrate (Axol C 62 Pellets from Degussa);
 proline derivatives, such as sodium palmitoyl proline (Sepicalm VG from Seppic), or the mixture of sodium palmitoyl sarcosinate, magnesium palmitoyl glutamate, palmitic acid and palmitoyl proline (Sepifeel One from Seppic);
 lactylates, such as sodium stearoyl lactylate (Akoline SL from Karlshamns AB);
 sarcosinates, such as sodium palmitoyl sarcosinate (Nikkol sarcosinate PN) or the 75/25 mixture of stearoyl sarcosine and myristoyl sarcosine (Crodasin SM from Croda);
 sulfonates, such as sodium C14-C17 alkyl sec sulfonate (Hostapur SAS 60 from Clariant);
 glycinates, such as sodium cocoyl glycinate (Amilite GCS-12 from Ajinomoto).

The compositions in accordance with the invention may also contain one or more amphoteric surfactants, for instance N-acylamino acids such as N-alkylaminoacetates and disodium cocoamphodiacetate, and amine oxides such as stearamine oxide, betaines, N-alkylamidobetaines and derivatives thereof, sultaines, alkyl polyaminocarboxylates, alkylamphoacetates, or else silicone surfactants, for instance dimethicone copolyol phosphates such as the product sold under the name Pecosil PS 100® by the company Phoenix Chemical, and mixtures thereof.

Preferably, the compositions according to the invention also comprise an amphiphilic silicone elastomer comprising polyoxyalkylene, in particular polyoxyethylene and/or polyoxypropylene, hydrophilic groups, blocks or grafts, or polyglycerol hydrophilic groups, blocks or grafts, and possibly having, in addition, alkyl side groups, in particular lauryl side groups, especially a polyglycerolated silicone elastomer. By way of example, use is made of an elastomeric crosslinked organopolysiloxane that can be obtained by means of a crosslinking addition reaction of a diorganopolysiloxane comprising at least one hydrogen bonded to the silicon and of polyglycerolated compounds having ethylenically unsaturated groups, in particular in the presence of a platinum catalyst.

As polyglycerolated silicone elastomers, use may be made of those sold under the names KSG-710, KSG-810, KSG-820, KSG-830 and KSG-840 by the company Shin Etsu.

Physiologically Acceptable Medium:

The term "physiologically acceptable medium" is intended to denote a medium which is particularly suitable for the application of a composition of the invention to the skin, the skin integuments (for instance hair, nails) or the lips.

The physiologically acceptable medium is generally suited to the nature of the support to which the composition must be applied, and also to the way in which the composition must be packaged. This medium may comprise at least one volatile silicone or organic solvent, this solvent preferably being compatible with the resins a) and b) and compatible with cosmetic use, as specified above.

The composition according to the invention may be in various forms, in particular in the form of powders (loose or compact), of an anhydrous composition, of a dispersion or of an emulsion, such as, in particular, a water/oil or water/wax emulsion, an oil/water emulsion, multiple emulsions or a wax/water emulsion, or else in the form of a gel.

A composition of the invention is preferably an emulsion, in particular a direct or inverse emulsion, or an anhydrous composition.

A dispersion can be carried out in the aqueous phase or in the oily phase.

An emulsion may have an oily or aqueous continuous phase.

Such an emulsion may be, for example, an inverse (W/O) or direct (O/W) emulsion, or else a multiple (W/O/W or O/W/O) emulsion.

In the case of the emulsions, inverse emulsions (W/O) are preferred.

An anhydrous composition is a composition containing less than 2% by weight of water, or even less than 0.5% of water, and which is in particular free of water. Where appropriate, such low amounts of water can in particular be introduced by ingredients of the composition which may contain residual amounts thereof.

The composition according to the invention may be in the form of a fluid, for example a pasty or liquid fluid. It may also be in the form of a loose or compact powder, of a soft paste or of a cream. For example, it may be an oil-in-water, water-in-oil or multiple emulsion, a solid emulsion, in particular of water-in-oil type, a solid or soft, in particular anhydrous, gel, in the form of a loose or compacted powder, and even in two-phase form.

The composition according to the invention is generally in the form of a composition for making up and/or caring for keratin materials, for example a foundation, in particular to be applied to the face or the neck, a concealer product, a complexion corrector, a tinted cream, a face powder, a lipstick, a lip balm, or a body makeup composition.

The composition according to the invention may comprise an aqueous phase.

The aqueous phase comprises water.

A water suitable for the invention may be a floral water such as cornflower water and/or a mineral water such as Vittel water, Lucas water or La Roche Posay water and/or a spring water.

The aqueous phase may also comprise organic solvents which are water-miscible (at ambient temperature –25° C.), for instance monoalcohols containing from 2 to 6 carbon atoms, such as ethanol or isopropanol; polyols containing in particular from 2 to 20 carbon atoms, preferably containing from 2 to 10 carbon atoms, and preferentially containing from 2 to 6 carbon atoms, such as glycerol, propylene glycol, butylene glycol, pentylene glycol, hexylene glycol, dipropylene glycol or diethylene glycol; glycol ethers (having in particular from 3 to 16 carbon atoms), such as mono-, di- or tripropylene glycol ($C_1$-$C_4$)alkyl ethers or mono-, di- or triethylene glycol ($C_1$-$C_4$)alkyl ethers, and mixtures thereof.

The aqueous phase may also comprise stabilizers, for example sodium chloride, magnesium dichloride and magnesium sulfate.

The aqueous phase may also comprise any water-soluble or water-dispersible compound that is compatible with an aqueous phase, such as gelling agents, film-forming polymers, thickeners or surfactants, and mixtures thereof.

In particular, a composition of the invention may comprise an aqueous phase in a content ranging from 1% to 80% by weight, in particular from 5% to 50%, and more particularly from 10% to 45% by weight, relative to the total weight of the composition.

According to another embodiment, a composition of the invention may be anhydrous.

An anhydrous composition may comprise less than 5% by weight of water, relative to the total weight of the composition, and in particular less than 3%, particularly less than 2%, and more particularly less than 1% by weight of water, relative to the total weight of the composition.

More particularly, an anhydrous composition may be devoid of water.

A cosmetic composition in accordance with the present invention may comprise at least one liquid and/or solid fatty phase.

In particular, a composition of the invention may comprise at least one liquid fatty phase, in particular at least one oil as mentioned above.

The term "oil" is intended to mean any fatty substance which is in liquid form at ambient temperature (20-25° C.) and at atmospheric pressure.

A composition of the invention may comprise a liquid fatty phase in a content ranging from 1% to 90%, in particular from 5% to 80%, in particular from 10% to 70%, and more particularly from 20% to 50% by weight, relative to the total weight of the composition.

The oily phase suitable for the preparation of the cosmetic compositions according to the invention may comprise hydrocarbon-based oils, silicone oils, fluoro or non-fluoro oils, or mixtures thereof.

The oils may be volatile or non-volatile as defined above.

According to one particular embodiment, the fatty phase of the composition according to the invention may contain only volatile compounds.

The composition according to the invention may also contain ingredients commonly used in the cosmetics industry, such as vitamins, thickeners, trace elements, softeners, sequestering agents, fragrances, basifying or acidifying agents, preservatives, sunscreens, surfactants, antioxidants, anti-hair loss agents, anti-dandruff agents, propellants, or mixtures thereof.

Of course, those skilled in the art will take care to select this or these optional additional compound(s), and/or the amount thereof, in such a way that the advantageous properties of the corresponding composition according to the invention are not, or not substantially, impaired by the addition envisioned.

A composition according to the invention may in particular be in the form of a composition for making up and/or caring for the skin, in particular a foundation.

According to another aspect, the invention also relates to a cosmetic assembly comprising:
i) a container delimiting at least one compartment, said container being closed by means of a closing member; and
ii) a composition placed inside said compartment, the composition being in accordance with the invention.

The container may be in any suitable form. It may in particular be in the form of a bottle, a tube, a jar, a case, a box, a sachet or a carton.

The closing member may be in the form of a removable stopper, a lid, a cap, a tear-off strip or a capsule, in particular of the type comprising a body attached to the container and a cover cap articulated on the body. It may also be in the form of a member for selectively closing the container, in particular a pump, a valve or a flap valve.

The container may be combined with an applicator, in particular in the form of a brush comprising an arrangement of bristles maintained by a twisted wire. Such a twisted brush is described in particular in U.S. Pat. No. 4,887,622. It may also be in the form of a comb comprising a plurality of application members, obtained in particular by molding. Such combs are described, for example, in patent FR 2 796 529. The applicator may be in the form of a fine brush, as described, for example, in patent FR 2 722 380. The applicator may be in the form of a block of foam or of elastomer, a felt or a spatula. The applicator may be free (tuft or sponge) or securely fastened to a rod borne by the closing member, as described, for example, in U.S. Pat. No. 5,492,426. The applicator may be securely fastened to the container, as described, for example, in patent FR 2 761 959.

The product may be contained directly in the container, or indirectly. By way of example, the product may be placed on an impregnated support, in particular in the form of a wipe or a pad, and placed (individually or as several together) in a box or in a sachet. Such a support incorporating the product is described, for example, in application WO 01/03538.

The closing member may be coupled to the container by screwing. Alternatively, the coupling between the closing member and the container is done other than by screwing, in particular via a bayonet mechanism, by click-fastening, gripping, welding, adhesive bonding or by magnetic attraction. The term "click-fastening" is intended to mean in particular any system involving the crossing of a bead or cord of material by elastic deformation of a portion, in particular the closing member, followed by a return to the elastically unconstrained position of said portion after the crossing of the bead or cord.

The container may be at least partially made of thermoplastic material. By way of examples of thermoplastic materials, mention may be made of polypropylene or polyethylene.

Alternatively, the container is made of non-thermoplastic material, in particular of glass or metal (or alloy).

The container may have rigid walls or deformable walls, especially in the form of a tube or a tubular bottle.

The container may comprise means for distributing or facilitating the distribution of the composition. By way of example, the container may have deformable walls so as to cause the composition to exit in response to a positive pressure inside the container, this positive pressure being caused by elastic (or nonelastic) squeezing of the walls of the container. Alternatively, in particular when the product is in the form of a stick, said product may be driven out by a piston mechanism. Still in the case of a stick, in particular of makeup product (foundation, etc.), the container may comprise a mechanism, in particular a rack mechanism, a threaded-rod mechanism or a helical groove mechanism, capable of moving a stick in the direction of said aperture. Such a mechanism is described, for example, in patent FR 2 806 273 or in patent FR 2 775 566. Such a mechanism for a liquid product is described in patent FR 2 727 609.

The container may consist of a carton with a base delimiting at least one housing containing the composition, and a lid, in particular articulated on the base, and capable of at least partially covering said base. Such a carton is described, for example, in application WO 03/018423 or in patent FR 2 791 042.

The container may be equipped with a drainer arranged in the region of the aperture of the container. Such a drainer makes it possible to wipe the applicator and optionally the rod to which it may be securely fastened. Such a drainer is described, for example, in patent FR 2 792 618.

The composition may be at atmospheric pressure inside the container (at room temperature) or pressurized, in particular by means of a propellant gas (aerosol). In the latter case, the container is equipped with a valve (of the type used for aerosols).

The content of all the patents or patent applications mentioned above is incorporated into the present application by way of reference.

The composition of the invention may be in the form of a care product or preferably a makeup product, which is in particular colored, for the skin, more specifically of the face, such as a foundation, a face powder, an eyeshadow, a face powder, an eyeshadow, a concealer product, a blusher, a loose or compacted powder, or else a body makeup product such as a semi-permanent tattooing product.

The composition according to the invention can be produced by known methods, generally used in the cosmetics field.

In the application, the contents, unless otherwise expressly mentioned, are expressed as weight relative to the total weight of the composition.

The aim of the following examples is to illustrate the compositions and methods according to this invention, but they in no way limit the scope of the invention. All the parts and percentages in the examples are by weight and all the measurements were obtained at approximately 23° C., unless otherwise indicated.

EXAMPLE NO. 1

Obtaining the Mixture of MQ and Propyl T Resins According to the Invention

Materials

MQ resin=an MQ resin of formula $M_{0.43}Q_{0.57}$ and of $M_n=3230$ dissolved in xylene at 70.8% by weight of solids. The MQ resin was produced according to the techniques described by Daudt in U.S. Pat. No. 2,676,182.

Propyl T resin=a propyl silsesquioxane resin at 74.8% by weight in toluene. The propyl silsesquioxane resin was obtained by hydrolysis of propyl trichlorosilane.

Various solutions of MQ resin and of propyl T resin are mixed in a three-necked flask equipped with a stirrer. Aliquots of each mixture are placed in an aluminum dish 2 inches in diameter, and heated under vacuum at a temperature of 110° C. for one hour, followed by 1 h 25 at 140° C. Visual qualitative observations regarding the clarity and the hardness of the mixtures obtained are made (see table 1 below):

TABLE 1

| Example # | MQ (g) | Propyl T (g) | Aliquot (g) | Dried aliquot (g) | % by weight of MQ resin | Clarity | Hardness |
|---|---|---|---|---|---|---|---|
| 1-a | 0.00 | 13.46 | 2.0475 | 1.5361 | 0.0 | Clear | Gum appearance; soft solid |
| 1-b | 1.40 | 12.03 | 2.0643 | 1.5415 | 9.9 | Clear | Soft solid |
| 1-c | 2.88 | 16.74 | 2.0840 | 1.5517 | 14.0 | Clear | Harder than 1-b |
| 1-d | 4.19 | 9.39 | 2.0746 | 1.5414 | 29.7 | Clear | Harder than 1-c |
| 1-e | 5.72 | 8.14 | 2.1066 | 1.5606 | 39.9 | Clear | Harder than 1-d |
| 1-f | 7.11 | 6.82 | 2.0257 | 1.4968 | 49.6 | Clear | Harder than 1-e |

The results obtained show the unexpected miscibility of the MQ resin and the propyl T resin, based on the clarity of the mixture without solvent and the increasing hardness as the amount of MQ resin increases.

According to an alternative referred to as 1-g, the mixture described in example 22 of application WO 2005/075567, in which the weight ratio between the MQ resin and the propyl T resin is 85/15, is used.

According to an alternative referred to as 1-h, the mixture of resins described in example 13 of application WO 2007/145765, in which the weight ratio between the MQ resin and the propyl T resin is 60/40, is used.

EXAMPLE 2

The following compositions were prepared (W/O emulsions).

| | INCI name | A | B | C | D |
|---|---|---|---|---|---|
| | | \multicolumn{4}{c}{Composition (%)} | | | |
| A1 | cetyl PEG/PPG-10/1 dimethicone (Abil EM90 from the company Goldschmidt) | 2.1 | 2.1 | 2.1 | 2.1 |
| | polyglyceryl-4 isostearate (ISOLAN GI34 ® by the company EVONIK GOLDSCHMIDT) | 2.8 | 2.8 | 2.8 | 2.8 |
| | hexyl laurate (Cetiol A from Cognis) | 2.1 | 2.1 | 2.1 | 2.1 |
| | Tristearin and Acetylated Glycol Stearate (Unitwix from the company United Guardian) | 1 | 1 | 1 | 1 |
| | Isododecane | 17.25 | 15.25 | 15.25 | 15.25 |
| | Disteardimonium Hectorite and Propylene Carbonate and isododecane (bentone gel ISD V from Elementis) | 5 | 5 | 5 | 5 |
| A2 | Isododecane | 3.5 | 3.5 | 3.5 | 3.5 |
| | 60/40 MQ/propyl T resin as described in example 1-h above | 8 | 8 | 8 | 8 |
| A3 | dicaprylyl carbonate (Cetiol CC from Cognis) | 5 | 5 | 5 | 5 |
| | CI 77492 Iron oxide and Disodium Stearoyl Glutamate and Aluminum Hydroxide (1) | 3.8 | 3.8 | 3.8 | 3.8 |
| | CI 77491 Iron oxide and Disodium Stearoyl Glutamate and Aluminum Hydroxide (2) | 1.2 | 1.2 | 1.2 | 1.2 |
| | CI 77499 Iron oxide And Disodium Stearoyl Glutamate and Aluminum Hydroxide (3) | 0.4 | 0.4 | 0.4 | 0.4 |
| | CI 77891 Titanium Dioxide and Disodium Stearoyl Glutamate and Aluminum Hydroxide (4) | 8.6 | 8.6 | 8.6 | 8.6 |
| A4 | Talc | | 4 | | 3 |
| | methyl methacrylate crosspolymer (PMMA) | | | 4 | 1 |
| B | Water/solvent | 37.15 | 35.15 | 35.15 | 35.15 |
| | Phenoxyethanol | 0.65 | 0.65 | 0.65 | 0.65 |
| | Methylparaben | 0.35 | 0.35 | 0.35 | 0.35 |
| | Magnesium sulfate | 0.65 | 0.65 | 0.65 | 0.65 |
| | Caprylyl glycol | 0.45 | 0.45 | 0.45 | 0.45 |
| | | 100 | 100 | 100 | 100 |

(1) 96.5% CI 77492 & 3.0% disodium stearoyl glutamate & 0.5% aluminum hydroxide, sold under the name NAI-C33-9001-10 by the company Miyoshi Kasei.
(2) 96.5% CI 77491 & 3.0% disodium stearoyl glutamate & 0.5% aluminum hydroxide, sold under the name NAI-C33-8001-10 by the company Miyoshi Kasei.
(3) 96.5% CI 77499 & 3.0% disodium stearoyl glutamate & 0.5% aluminum hydroxide, sold under the name NAI-C33-7001-10 by the company Miyoshi Kasei.
(4) 97% CI 77891 & 2.5% disodium stearoyl glutamate & 0.5% aluminum hydroxide, sold under the name NAI-TAO-77891 by the company Miyoshi Kasei.
Composition A: Example without filler
Composition B: Example with talc (lamellar mineral filler)
Composition C: Example with PMMA (round organic filler)
Composition D: Example with talc + PMMA (mineral filler + organic filler) combination Procedure The constituents of phase A3 are weighed out. The mixture is passed through a triple roll mill.

The constituents of phase A1 are then weighed into the main beaker and it is placed in a waterbath (75-80° C.). When the mixture is homogeneous, the constituents of phase A2 are added. After stirring for 5 minutes on a Moritz stirrer at 1500 rpm, the mixture is cooled to ambient temperature.

A3 is incorporated into the phase A1+A2, with stirring on a Moritz stirrer at 1500 rpm.

The constituents of phase A4 are then added successively, while keeping the same stirring.

The constituents of phase B are weighed out. Phase B is brought to boiling, until complete dissolution of the constituents. Phase B is cooled to 50° C.

Phase B is then trickled into the phase A1+A2+A3+A4, with stirring on a Moritz stirrer at 3200 rpm. The stirring is maintained for a minimum of 10 minutes.

Protocol for Instrumental Measurements of the Immediate Color and Staying Power of the Color A colorimetric measurement of the skin is carried out before and after applying makeup by measuring the red, yellow and brightness indices, respectively a*, b*, L*. For each woman, an image is taken using a chromasphere, with a definition of 410×410 pixels.

The results are expressed in the following way. The color is quantified by the red, yellow and brightness indices analyzed by the camera (respectively a*, b*, L*). The staying power of the color is calculated by the variation in these variables after the makeup has been worn for 3 hours (deltaE94).

More specifically, the measurements are carried out on a panel of individuals who are kept in an air-conditioned (22° C.+/−2° C.) waiting room for 15 min before the beginning of the test. They remove their makeup and an image of one of their cheeks is acquired using the chromasphere with a definition of 410×410 pixels. This image makes it possible to measure the color at T0 before applying makeup. Approximately 100 mg of cosmetic composition are then weighed out into a watch glass and are applied with the bare fingers to the half of the face on which the T0 measurement was carried out.

After a drying time of 15 min, an image of the made-up cheek is acquired using the chromasphere. This image makes it possible to measure the color immediately after applying makeup (Timm). The models then return to the air-conditioned room for 3 h. Finally, an image of the made-up cheek after waiting for 3 h is acquired using the chromasphere. This image makes it possible to measure the color after wearing makeup for 3 h (T3h).

The results are expressed by calculating the difference (Timm−T0), which measures the effect of the makeup. The difference (T3h−Timm) measuring the staying power of this effect is then calculated. Each image obtained using the camera is made use of in color. The color is quantified by the red and yellow indices, the brightness and the color difference (respectively a*,b*,L and deltaE). The deltaE, dE or else ΔE is defined as a measurement of difference between two colors. The formula established in 1976 is shown below:

$$|\Delta E^*| = \sqrt{|(L_1-L_2)^2 + (a_1-a_2)^2 + (b_1-b_2)^2|}$$

where:

$L_1$, $a_1$ and $b_1$ are the coordinates in the colorimetric space of the first color to be compared and $L_2$, $a_2$ and $b_2$ those of the second.

Protocol for Instrumental Measurements of the Immediate Mattness and the Persistence of the Mattness Protocol for instrumental measurements of the immediate mattness and the persistence of the mattness The mattness effect and staying power of the mattness of the application, to the skin of a panel of individuals, of the W/O emulsion described above is evaluated. The mattness and the staying power of the mattness can be measured by means of the protocol described hereinafter. The mattness of a region of the skin, for example of the face, is measured using a polarimetric camera, which is a black and white polarimetric imaging system, with which images are acquired in parallel (P) and crossed (C) polarized light. By analyzing the image resulting from the subtraction of the two images (P-C), the shine is quantified by measuring the mean level of gray of the 5% of shiniest pixels corresponding to the regions of shine.

More specifically, the measurements are carried out on a panel of individuals who are kept in an air-conditioned (22° C.+/−2° C.) waiting room for 15 min before the beginning of the test. They remove their makeup and an image of one of their cheeks is acquired with the polarimetric camera. This image makes it possible to measure the shine at T0 before applying makeup. Approximately 100 mg of the composition described above are then weighed out into a watch glass and are applied with the bare fingers to the half of the face on which the T0 measurement was carried out.

After a drying time of 15 min, an image of the made-up cheek is acquired with the polarimetric camera. This image makes it possible to measure the shine immediately after applying makeup (Timm). The models then return to the air-conditioned room for 3 h. Finally, an image of the made-up cheek after waiting 3 h is acquired with the polarimetric camera. This image makes it possible to measure the shine after wearing makeup for 3 h (T3h). The results are expressed by calculating the difference (Timm−T0), which measures the effect of the makeup. A negative value means that the makeup reduces the shine of the skin and that it is thus mattifying.

The difference (T3h−Timm) measuring the staying power of this effect is then calculated. The value obtained should be as low as possible, which means that the mattness of the makeup does not change over time.

Protocol for Instrumental Measurements of the Immediate Uniformity and Staying Power of the Uniformity A colorimetric measurement of the skin before and after applying makeup is carried out by measuring the means for the planes a* (green-red), b*(blue-yellow), L*(brightness). For each woman, an image is taken using a chromasphere with a definition of 410×410 pixels. More specifically, the measurements are carried out on a panel of individuals who are kept in an air-conditioned (22° C.+/−2° C.) waiting room for 15 min before the beginning of the test. They remove their makeup and an image of one of their cheeks is acquired using the chromasphere with a definition of 410×410 pixels. This image makes it possible to measure the color at T0 before applying makeup. Approximately 100 mg of cosmetic composition are then weighed out into a watch glass and are applied with the bare fingers to the half of the face on which the measurement was carried out at T0.

After a drying time of 15 min, an image of the made-up cheek is acquired using the chromasphere. This image makes it possible to measure the color immediately after applying makeup (Timm). The models then return to the air-conditioned room for 3 h. Finally, an image of the made-up cheek after waiting for 3 h is acquired using the chromasphere. This image makes it possible to measure the color after wearing makeup for 3 h (T3h).

Each image obtained using the camera is made use of by coxellography. The standard deviation of each monochrome plane is calculated. The product of the three standard deviations is equal to the coxellographic index. This parameter is used for the statistical calculations. The more uniform the skin, the lower the standard deviation. The coxellographic index changes in the same way since it is the product of the standard deviations of the three planes a*, b* and L*.

Staying Power Results

For the measurements carried out, it is considered that:
+ slight effect or low staying power
++ moderate effect or moderate staying power
+++ significant effect or good staying power
++++ very significant effect or very good staying power

| Compositions | A (without filler) | B (talc) | C (PMMA) | D (talc + PMMA) |
|---|---|---|---|---|
| Mattifying effect | ++ | ++ | +++ | ++++ |
| Mattness staying power performance | ++ | + | +++ | ++ |
| Color staying power performance | ++++ | ++++ | + | ++++ |
| Uniforming effect | ++++ | ++ | ++ | + |
| Uniformity staying power performance | ++ | ++++ | ++++ | ++++ |

Composition D exhibits a mattifying effect at Timm which is very high compared with the other compositions, and a mattness staying power which is judged to be moderate at 3 hours (but greater than that of composition B). In comparison with formulation C, which has better staying power but much less of a mattifying effect at Timm, the mattness at 3 hours is equivalent.

After 3 hours, the color staying power is excellent on this formulation, and significantly better than that of composition C. The uniforming effect is low but has very good staying power over time.

According to these results, it can be argued that there is good overall staying power (in terms of mattness, color and uniformity), with a level of mattifying which is much greater than that of compositions A, B and C.

Sensory Evaluation Results (Makeup Application in the Laboratory)

On application, compositions B and D dry less quickly than the other compositions.

Composition A catches during application and dries too quickly. A sensation of rubbing is felt on the skin, which makes the application uncomfortable and unpleasant.

Composition B does not dry too quickly, but crunches under the fingers on application. It gives a result which is perceived as satin-like or even shiny.

Composition C dries more quickly. It is thicker under the fingers, presents more material.

Composition D emerges as being finer on application, with better glidance. Application is easy with no "crunching" effect on the skin. The product glides perfectly under the fingers, which makes application pleasant.

The combination according to the invention (composition D) therefore makes it possible to provide good staying-power properties (in particular color and uniformity) with a very high level of mattifying, and very good cosmetic performance levels.

Compositions are reproduced according to this example, in which compositions the 60/40 mixture of MQ/propyl T resins according to example 1-h described above is replaced with the mixture of MQ/propyl T resins according to example 1-f described above, comprising an MQ/propyl T weight ratio of approximately 50/50, and similar results are obtained with said compositions.

The invention claimed is:

1. A composition, comprising, in a physiologically acceptable medium:
   a) a siloxane resin comprising at least 80 mol % of units
      (i) at least one M unit of formula $(R'_3SiO_{1/2})_a$, and
      (ii) at least one Q unit of formula $(SiO_{4/2})_b$,
   wherein R' independently represents an alkyl group comprising from 1 to 8 carbon atoms, an aryl group, a carbinol group, or an amino group, with the condition that at least 95 mol % of the R' groups are alkyl groups,
   wherein a and b are values greater than 0, and
   wherein a ratio a/b is between 0.5 and 1.5;
   b) a film-forming propyl silsesquioxane resin comprising at least 80 mol % of at least one T unit of formula $R"SiO_{3/2}$, wherein R" independently represents an alkyl group comprising from 1 to 8 carbon atoms, an aryl group, a carbinol group, or an amino group, with the condition that at least 40 mol % of the R" groups are propyl groups,
   wherein a weight ratio between the resins a) and b) is between 1/99 and 99/1,
   wherein the resins a) and b) are not bonded to one another via covalent bonds, and
   wherein a number of M units in the final mixture is less than a number of T+Q units;
   c) a mineral filler that is talc; and
   d) an organic filler that is polymethyl methacrylate (PMMA).

2. A cosmetic assembly, comprising:
   i. a container delimiting at least one compartment, wherein the container is closed by a closing member; and
   ii. the composition of claim 1, placed inside the at least one compartment.

3. The cosmetic assembly of claim 2, further comprising:
   iii. an applicator in the form of a block of foam or elastomer, a felt, or a spatula.

4. A cosmetic method for at least one of making up a keratin material and caring for a keratin material, the method comprising applying, to the keratin material a composition comprising, in a physiologically acceptable medium:
   a) a siloxane resin comprising at least 80 mol % of units
      (i) at least one M unit of formula $(R'_3SiO_{1/2})_a$, and
      (ii) at least one Q unit of formula $(SiO_{4/2})_b$,
   wherein R' independently represents an alkyl group comprising from 1 to 8 carbon atoms, an aryl group, a carbinol group, or an amino group, with the condition that at least 95 mol % of the R' groups are alkyl groups,
   wherein a and b are values greater than 0, and
   wherein a ratio a/b is between 0.5 and 1.5;
   b) a film-forming propyl silsesquioxane resin comprising at least 80 mol % of at least one T unit of formula $R"SiO_{3/2}$, wherein R" independently represents an alkyl group comprising from 1 to 8 carbon atoms, an aryl group, a carbinol group, or an amino group, with the condition that at least 40 mol % of the R" groups are propyl groups,
   wherein a weight ratio between the resins a) and b) is between 1/99 and 99/1,
   wherein the resins a) and b) are not bonded to one another via covalent bonds, and
   wherein a number of M units in the final mixture is less than a number of T+Q units; and
   c) a mineral filler and an organic filler, wherein the mineral filer is talc and the organic filler is polymethyl methacrylate (PMMA).

5. The method of claim 4, wherein the siloxane and propyl silsesquioxane resins a) and b) are formulated in the composition via a mixture obtained by a method comprising:
   mixing a solution of the siloxane resin with a solution of the propyl silsesquioxane resin; then
   heating uniformly for at least one hour at a single temperature or at temperature holds of between 90° C. and 250° C.,
   wherein the heating is carried out without the presence of a catalyst for chemical condensation between the two resins.

6. The method of claim 4, wherein the composition is an emulsion or an anhydrous composition.

7. The method of claim 4, wherein the composition comprises an amount of siloxane resins a) and b), with respect to active material, measured as dry matter, ranging from 0.5% to 60% by weight, relative to the total weight of the composition.

8. The method of claim 4, wherein the filler(s) is or are present in the composition in a content ranging from 0.01% to 50% by weight.

9. A composition, comprising, in a physiologically acceptable medium:
   a) a siloxane resin comprising at least 80 mol % of units
      (i) at least one M unit of formula $(R'_3SiO_{1/2})_a$, and
      (ii) at least one Q unit of formula $(SiO_{4/2})_b$,
   wherein R' independently represents an alkyl group comprising from 1 to 8 carbon atoms, an aryl group, a carbinol group, or an amino group, with the condition that at least 95 mol % of the R' groups are alkyl groups,
   wherein a and b are values greater than 0, and
   wherein a ratio a/b is between 0.5 and 1.5;
   b) a propyl silsesquioxane resin comprising at least 80 mol % of at least one T unit of formula $R''SiO_{3/2}$, wherein R'' independently represents an alkyl group comprising from 1 to 8 carbon atoms, an aryl group, a carbinol group, or an amino group, with the condition that at least 80 mol % of the R'' groups are propyl groups;
   wherein a weight ratio between the resins a) and b) is between 1/99 and 99/1,
   wherein the resins a) and b) are not bonded to one another via covalent bonds, and
   wherein a number of M units in a final mixture of the composition is less than a number of T+Q units;
   c) a mineral filler that is talc; and
   d) an one organic filler that is polymethyl methacrylate (PMMA).

10. A cosmetic assembly, comprising:
   a container delimiting at least one compartment, wherein the container is closed by a closing member; and
   ii. the composition of claim 9, placed inside the at least one compartment.

11. The cosmetic assembly of claim 10, further comprising:
   iii. an applicator in the form of a block of foam or elastomer, a felt, or a spatula.

12. A cosmetic method for at least one of making up skin and caring for skin, the method comprising contacting with the skin a composition comprising, in a physiologically acceptable medium:
   a) a siloxane resin comprising at least 80 mol % of units
      (i) at least one M unit of formula $(R'_3SiO_{1/2})_a$, and
      (ii) at least one Q unit of formula $(SiO_{4/2})_b$,
   wherein R' independently represents an alkyl group comprising from 1 to 8 carbon atoms, an aryl group, a carbinol group, or an amino group, with the condition that at least 95 mol % of the R' groups are alkyl groups,
   wherein a and b are values greater than 0, and
   wherein a ratio a/b is between 0.5 and 1.5;
   b) a propyl silsesquioxane resin comprising at least 80 mol % of at least one T unit of formula $R''SiO_{3/2}$, wherein R'' independently represents an alkyl group comprising from 1 to 8 carbon atoms, an aryl group, a carbinol group, or an amino group, with the condition that at least 80 mol % of the R'' groups are propyl groups;
   wherein a weight ratio between the resins a) and b) is between 1/99 and 99/1,
   wherein the resins a) and b) are not bonded to one another via covalent bonds, and
   wherein a number of M units in a final mixture of the composition is less than a number of T+Q units;
   and
   c) a mineral filler and an organic filler, wherein the mineral filer is talc and the organic filler is polymethyl methacrylate (PMMA).

13. The method of claim 12, wherein the siloxane and propyl silsesquioxane resins a) and b) are formulated in the composition via a mixture obtained by a method comprising:
   mixing a solution of the siloxane resin with a solution of the propyl silsesquioxane resin; then
   heating uniformly for at least one hour at a single temperature or at temperature holds of between 90° C. and 250° C.,
   wherein the heating is carried out without the presence of a catalyst for chemical condensation between the two resins.

14. The method of claim 12, wherein the composition is an emulsion or an anhydrous composition.

15. The method of claim 12, wherein the composition comprises an amount of siloxane resins a) and b), with respect to active material, measured as dry matter, ranging from 0.5% to 60% by weight, relative to the total weight of the composition.

16. The method of claim 12, wherein the filler(s) is or are present in the composition in a content ranging from 0.01% to 50% by weight.

* * * * *